US010100368B2

(12) United States Patent
Driebe et al.

(10) Patent No.: US 10,100,368 B2
(45) Date of Patent: Oct. 16, 2018

(54) METHODS, KITS, AND COMPOSITIONS FOR DETECTION OF MRSA

(75) Inventors: Elizabeth Driebe, Flagstaff, AZ (US); David Engelthaler, Flagstaff, AZ (US); Jolene Bowers, Flagstaff, AZ (US); Paul Keim, Flagstaff, AZ (US)

(73) Assignees: The Translational Genomics Research Institute, Phoenix, AZ (US); Arizona Board of Regents on behalf of Northern Arizona University, Flagstaff, AZ (US)

( * ) Notice: Subject to any disclaimer, the term of this patent is extended or adjusted under 35 U.S.C. 154(b) by 1570 days.

(21) Appl. No.: 13/051,755

(22) Filed: Mar. 18, 2011

(65) Prior Publication Data

US 2011/0312504 A1 Dec. 22, 2011

Related U.S. Application Data

(60) Provisional application No. 61/315,664, filed on Mar. 19, 2010, provisional application No. 61/432,511, filed on Jan. 13, 2011.

(51) Int. Cl.
*C12Q 1/68* (2018.01)
*C12Q 1/689* (2018.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS

| 6,773,882 B2 * | 8/2004 | Hogan ............... C12Q 1/6895 435/471 |
| 2004/0241824 A1 | 12/2004 | Schrenzel et al. |
| 2007/0031850 A1 | 2/2007 | Mounts et al. |
| 2008/0031889 A1 | 2/2008 | Doucette-Stamm et al. |
| 2009/0035780 A1 | 2/2009 | McCarthy et al. |
| 2009/0068641 A1 | 3/2009 | Bergeron et al. |
| 2009/0111134 A1 | 4/2009 | Zhang et al. |

FOREIGN PATENT DOCUMENTS

| WO | WO02082086 | 10/2002 |
| WO | WO 2005014857 | 2/2005 |
| WO | WO 2009086218 | 7/2009 |

OTHER PUBLICATIONS

Diffenbach (PCR methods and Applications (1993) vol. 3, pp. S30-S37).*
Roux et al (PCR Methods and Applications (1995) vol. 4, pp. s185-s194).*
Sakai et al. (Journal of Clinical Microbiology 2004 vol. 42 p. 5739).*
Martineau et al. (Journal of clinical microbiology 2001 vol. 39 p. 2541).*
Patent Examination Report No. 1, Australian Government IP Australia, dated Apr. 3, 2014.
Search Report from the European Patent Office for Application No. 11757080.4 dated Sep. 27, 2013.
McDonald Ryan R. et al "Development of a triplex real-time PCR assay for detection of Panton-Valentine leukocidin toxin genes in clinical isolates of methicillin-resistant *Staphylococcus aureus*" Journal of Clinical Microbiology, American Society for Microbiology US vol. 43 No. 12, 6147-6149 Dec. 1, 2005.
Louie L et al. "Rapid detection of methicillin-resistant staphylococci from blood culture bottles using a multiplex PCR assay" Journal of Clinical Microbiology, American Society for Microbiology US vol. 40 No. 8 2786-2790 Aug. 1, 2002.
Lem P et al. "Direct Detection of mecA, nuc and 16s rRNA genes in BacT/Alert blood culture bottles" Diagnostic Microbiology and Infectious Diseases, Elsevier Science Publishing Group NL vol. 41 No. 3 165-168 Nov. 1, 2001.
Paule S M et al. "Real-time PCR can rapidly detect methicillin-susceptible and methicillin-resistant *Staphylococcus aureus* directly from positive blood culture bottles" American Journal of Clinical Pathology US vol. 124 404-407 2005.
Maes N et al. "Evaluation of a triplex PCR assay to discriminate *Staphylococcus aureus* from coagulase-negative Staphylococci and determine methicillin resistance from blood cultures" Journal of Clinical Microbiology, American Society for Microbiology US vol. 40 No. 4 1514-1517 Apr. 1, 2002.
Lindsey W C et al. "Development of a rapid diagnostic assay for methicillin-resistant *Staphylococcus aureus* and methicillin-resistant coagulase-negative *Staphylococcus*" Diagnostic Microbiology and Infectious Diseases, Elsevier Science Publishing Co. NL vol. 61 No. 3 273-279 Jul. 1, 2008.
Fang H and Hedin G "Rapid screening and identification of methicillin-resistant *Staphylococcus aureus* from clinical samples by selective-broth and real-time PCR assay" Journal of Clinical Microbiology vol. 41 No. 7 2894-2899 Jul. 2003.
Fosheim G E et al. "Multiplex real-time PCR assay for detection of methicillin-resistant *Staphylococcus aureus* and associated toxin genes" Journal of Clinical Microbiology US vol. 49 No. 8 Aug. 2011.
Kilic et al., Triplex real-time polymerase chain reaction assay for simultaneous detection of *Staphylococcus aureus* and coagulase-negative staphylocci and determination of methicillin resistance directly from positive blood culture bottles Diag. Microbiol. Dis. Mar. 10, 2010 66(4): 349-355.
International Search Report and Written Opinion for PCT application Serial No. PCT/US11/29043 dated Jun. 6, 2011.
International Preliminary Report on Patentability for PCT application Serial No. PCT/US11/29043 dated Sep. 25, 2012.

* cited by examiner

*Primary Examiner* — Katherine D Salmon
(74) *Attorney, Agent, or Firm* — Rodney J. Fuller; Booth Udall Fuller, PLC

(57) ABSTRACT

The present invention provides multiplex assays, methods and kits that may be used to detect and confirm the presence of MRSA in a sample. The methods include real-time PCR assays, and the kits and compositions include oligonucleotides used as primers and probes. The present invention further comprises assays useful to identify and differentiate MRSA, MSSA, MRSE, MSSE, MRCNS and MSCNS in a sample.

19 Claims, 13 Drawing Sheets
Specification includes a Sequence Listing.

SEQUENCE LISTING

```
<160> NUMBER OF SEQ ID NOS: 30

<210> SEQ ID NO 1
<211> LENGTH: 23
<212> TYPE: DNA
<213> ORGANISM: Artificial
<220> FEATURE:
<223> OTHER INFORMATION: nuc forward

<400> SEQUENCE: 1
ccaagccttg acgaactaaa gct                                              23

<210> SEQ ID NO 2
<211> LENGTH: 23
<212> TYPE: DNA
<213> ORGANISM: Artificial
<220> FEATURE:
<223> OTHER INFORMATION: nuc reverse

<400> SEQUENCE: 2
ggtcctgaag caagtgcatt tac                                              23

<210> SEQ ID NO 3
<211> LENGTH: 29
<212> TYPE: DNA
<213> ORGANISM: Artificial
<220> FEATURE:
<223> OTHER INFORMATION: nuc probe

<400> SEQUENCE: 3
cagcataaat atacgctaag ccacgtcca                                        29

<210> SEQ ID NO 4
<211> LENGTH: 20
<212> TYPE: DNA
<213> ORGANISM: Staphylococcus aureus
<220> FEATURE:
<221> NAME/KEY: misc_feature
<223> OTHER INFORMATION: femA forward
```

```
<400> SEQUENCE: 4
tcaaatcgcg gtccagtgat                                              20

<210> SEQ ID NO 5
<211> LENGTH: 25
<212> TYPE: DNA
<213> ORGANISM: Staphylococcus aureus
<220> FEATURE:
<221> NAME/KEY: misc_feature
<223> OTHER INFORMATION: femA reverse

<400> SEQUENCE: 5
attacctgta atctcgccat catga                                        25

<210> SEQ ID NO 6
<211> LENGTH: 24
<212> TYPE: DNA
<213> ORGANISM: Staphylococcus aureus
<220> FEATURE:
<221> NAME/KEY: misc_feature
<223> OTHER INFORMATION: femA probe

<400> SEQUENCE: 6
catcgttgtc tatacctaca tatc                                         24

<210> SEQ ID NO 7
<211> LENGTH: 23
<212> TYPE: DNA
<213> ORGANISM: Staphylococcus epidermidis
<220> FEATURE:
<221> NAME/KEY: misc_feature
<223> OTHER INFORMATION: femA forward

<400> SEQUENCE: 7
gctggtggaa cttcaaatcg tta                                          23

<210> SEQ ID NO 8
<211> LENGTH: 27
<212> TYPE: DNA
<213> ORGANISM: Staphylococcus epidermidis
<220> FEATURE:
<221> NAME/KEY: misc_feature
<223> OTHER INFORMATION: femA reverse

<400> SEQUENCE: 8
cgattaatac catgttcaat tgcatag                                      27

<210> SEQ ID NO 9
<211> LENGTH: 24
<212> TYPE: DNA
<213> ORGANISM: Staphylococcus epidermidis
<220> FEATURE:
<221> NAME/KEY: misc_feature
<223> OTHER INFORMATION: femA probe

<400> SEQUENCE: 9
tttgcaggga gctatgcggt tcaa                                         24

<210> SEQ ID NO 10
<211> LENGTH: 32
<212> TYPE: DNA
<213> ORGANISM: Artificial
<220> FEATURE:
<223> OTHER INFORMATION: tuf S. aureus forward

<400> SEQUENCE: 10
```
agaattaatg gaagctgtag atacttacat tc                                32

<210> SEQ ID NO 11
<211> LENGTH: 31
<212> TYPE: DNA
<213> ORGANISM: Artificial
<220> FEATURE:
<223> OTHER INFORMATION: tuf S. aureus reverse

<400> SEQUENCE: 11
ctgtaacagt tgttttagat gtgtcatgta a                                 31

<210> SEQ ID NO 12
<211> LENGTH: 30
<212> TYPE: DNA
<213> ORGANISM: Artificial
<220> FEATURE:
<223> OTHER INFORMATION: tuf S. aureus probe

<400> SEQUENCE: 12
ctccagaacg tgattctgac aaaccattca                                   30

<210> SEQ ID NO 13
<211> LENGTH: 24
<212> TYPE: DNA
<213> ORGANISM: Artificial
<220> FEATURE:
<223> OTHER INFORMATION: tuf CNS forward

<400> SEQUENCE: 13
gctcaaaaga acatgccaat attg                                         24

<210> SEQ ID NO 14
<211> LENGTH: 25
<212> TYPE: DNA
<213> ORGANISM: Artificial
<220> FEATURE:
<223> OTHER INFORMATION: tuf CNS reverse

<400> SEQUENCE: 14
taatacagtt gcgatagcag ctgtt                                        25

<210> SEQ ID NO 15
<211> LENGTH: 30
<212> TYPE: DNA
<213> ORGANISM: Artificial
<220> FEATURE:
<223> OTHER INFORMATION: tuf CNS probe

<400> SEQUENCE: 15
aaagtwgttt taccatggtc aacgtgaccg                                   30

<210> SEQ ID NO 16
<211> LENGTH: 24
<212> TYPE: DNA
<213> ORGANISM: methycillin resistant staphylococcus aureus
<220> FEATURE:
<221> NAME/KEY: misc_feature
<223> OTHER INFORMATION: mecA forward

<400> SEQUENCE: 16
ggaacgatgc ctatctcata tgct                                         24

<210> SEQ ID NO 17
<211> LENGTH: 25
<212> TYPE: DNA

```
<213> ORGANISM: methycillin resistant staphylococcus aureus
<220> FEATURE:
<221> NAME/KEY: misc_feature
<223> OTHER INFORMATION: mecA reverse

<400> SEQUENCE: 17
atagcgtcat tattccagga atgca                                            25

<210> SEQ ID NO 18
<211> LENGTH: 26
<212> TYPE: DNA
<213> ORGANISM: methycillin resistant staphylococcus aureus
<220> FEATURE:
<221> NAME/KEY: misc_feature
<223> OTHER INFORMATION: mecA probe

<400> SEQUENCE: 18
ttggccaatt ccacattgtt tcggtc                                           26

<210> SEQ ID NO 19
<211> LENGTH: 687
<212> TYPE: DNA
<213> ORGANISM: Staphylococcus aureus
<220> FEATURE:
<221> NAME/KEY: misc_feature
<223> OTHER INFORMATION: nuc sequence

<400> SEQUENCE: 19
atgacagaat acttattaag tgctggcata tgtatggcaa ttgtttcaat attacttata      60
gggatggcta tcagtaatgt ttcgaaagaa caatacgcaa agaggttttt cttttcgct     120 actagttgct tagtgttaac tttagttgta gcttcaagtc taagtagctc agcaaatgca    180
tcacaaacag ataatggcgt aaatagaagt ggttctgaat atccaacagt atatagtgca    240
acttcaacta aaaaattaca taaagaacct gcgacattaa ttaaagcgat tgatggtgat    300
actgttaaat taatgtacaa aggtcaacca atgacattca gactattatt ggttgataca    360
cctgaaacaa agcatcctaa aaaaggtgta gagaaatatg gtcctgaagc aagtgcattt    420
acgaaaaaga tggtagaaaa tgcaaagaaa attgaagtcg agtttgacaa aggtcaaaga    480
actgataaat atggacgtgg cttagcgtat atttatgctg atggaaaaat ggtaaacgaa    540
gctttagttc gtcaaggctt ggctaaagtt gcttatgttt ataaacctaa caatacacat    600
gaacaacttt taagaaaaag tgaagcacaa gcgaaaaaag agaaattaaa tatttggagc    660
gaagacaacg ctgattcagg tcaataa                                        687

<210> SEQ ID NO 20
<211> LENGTH: 1263
<212> TYPE: DNA
<213> ORGANISM: Staphylococcus aureus
<220> FEATURE:
<221> NAME/KEY: misc_feature
<223> OTHER INFORMATION: femA sequence

<400> SEQUENCE: 20
atgaagttta caaatttaac agctaaagag tttggtgcct ttacagatag catgccatac     60
agtcatttca cgcaaactgt tggccactat gagttaaagc ttgctgaagg ttatgaaaca    120
catttagtgg gaataaaaaa caataataac gaggttattg cagcttgctt acttactgct    180
gtacctgtta tgaaagtgtt caagtatttt tattcaaatc gcggtccagt gatcgattat    240
gaaaatcaag aactcgtaca cttttctctt aatgaattat caaatatgt taaaaaacat    300 cgttgtctat acctacatat cgatccatat ttaccatatc aatacttgaa tcatgatggc    360
```

```
gagattacag gtaatgctgg taatgattgg ttctttgata aaatgagtaa cttaggattt      420
gaacatactg gattccataa aggatttgat cctgtgctac aaattcgtta tcactcagtg      480
ttagatttaa aagataaaac agcagatgac atcattaaaa atatggatgg acttagaaaa      540
agaaacacga aaaaagttaa aagaatggt gttaaagtaa gatatttatc tgaagaagaa       600
ctaccaattt ttagatcatt tatggaagat acgtcagaat caaaagcttt tgctgatcgt      660
gatgacaagt tttattacaa tcgcttaaaa tattacaaag agcgtgtgtt agtgcccttta     720 gcgtatatca attttgatga atatattaaa gaactaaatg aagagcgtga tattttaaat     780
aaagatttaa ataaagcatt aaaggatatt gaaaaacgtc ctgaaaataa aaaagcacat     840
aacaagcgag ataacttaca acaacaactt gatgcaaatg agcaaaagat tgaagaaggt     900
aaacgtcttc aagaagaaca tggtaatgaa ttacctatct ctgctggttt cttctttatc     960
aatccatttg aagttgttta ttatgctggt ggtacatcaa atgcattccg tcattttgcc    1020
ggaagttatg cagtgcaatg ggaaatgatt aattatgcat taaatcatgg cattgaccgt    1080
tataatttct atggtgttag tggtaaattt acagaagatg ctgaagatgc tggtgtagtt    1140
aaattcaaaa aaggttacaa tgctgaaatt attgaatatg ttggtgactt tattaaacca    1200
attaataaac ctgtttacgc agcatatacc gcacttaaaa aagttaaaga cagaattttt    1260
tag                                                                  1263

<210> SEQ ID NO 21
<211> LENGTH: 1254
<212> TYPE: DNA
<213> ORGANISM: Staphylococcus epidermidis
<220> FEATURE:
<221> NAME/KEY: misc_feature
<223> OTHER INFORMATION: femA sequence

<400> SEQUENCE: 21
atgaagttta cgaatttgac agctaaagaa tttagtgact ttactgatcg tatgacatat       60
agtcatttta cacaaatgga aggtaattac gaattaaagg ttgctgaagg taccgagtca      120
catttagttg gaattaaaaa taatgataac gaagtgattg cagcttgttt attaacagct      180
gttcctgtaa tgaaaatatt taaatatttt tattccaatc gcggtccagt aatagattat      240
aataataaag agcttgtaca ttttttcttt aatgaattga gtaaatatgt aaaaaaatat      300
aattgtttat atttaagagt tgacccatac cttccatatc aatatttaaa tcatgaggga     360
gaaataactg gaaatgcagg tcatgattgg attttgatg aattagagag tttaggatat      420
aaacacgaag gattccacaa aggatttgat cctgtattac aaatccgata tcattctgtt      480
ctaaatttag caaacaaaag tgctaatgat gtttaaaaa acatggatgg tttaagaaag      540
cgtaatacta aaaaagttaa gaaaaatgga gttaaagtcc gcttttatc tgaagaagag      600 ttacctatat ttaggtcatt tatggaggat acctctgaaa ctaaagattt tgcagataga     660
gaagatagtt tttattacaa cagattcaaa cattataaag accgtgtttt agtaccacta     720
gcctatatta actttgatga gtatatagag gaactaaata tgaaagaaa tgtgcttaat      780 aaagattata ataagcttt aaaagacatt gagaaacgtc cagagaataa aaaagcacat     840
aacaaaaagg aaaatttaga acaacaactc gatgcaaatc agcaaaaaat taatgaagct     900 aaaacttaa aacaagaaca tggcaatgaa ttacccatct ctgctggctt cttataatt     960 aatccgtttg aagtagttta ctacgctggt ggaacttcaa atcgttatcg ccattttgca    1020
gggagctatg cggttcaatg gaagatgatt aactatgcaa ttgaacatgg tattaatcgg    1080
```

```
tataatttct atggtattag tggtgacttt agtgaagatg ctgaagatgc tggcgtagtt      1140
aagtttaaaa agggctatga tgccgatgtt atagaatacg ttggtgactt tattaaacct      1200
attaataaac caatgtataa catttataga acacttaaaa aactaaagaa atag            1254
```

<210> SEQ ID NO 22
<211> LENGTH: 1185
<212> TYPE: DNA
<213> ORGANISM: Staphylococcus aureus
<220> FEATURE:
<221> NAME/KEY: misc_feature
<223> OTHER INFORMATION: tuf sequence

<400> SEQUENCE: 22

```
atggcaaaag aaaaattcga tcgttctaaa gaacatgcca atatcggtac tatcggtcac        60
gttgaccatg gtaaaacaac attaacagca gcaatcgcta ctgtattagc aaaaaatggt       120
gactcagttg cacaatcata tgacatgatt gacaacgctc cagaagaaaa agaacgtggt       180
atcacaatca atacttctca cattgagtac caaactgaca aacgtcacta cgctcacgtt       240
gactgcccag acacgctga ctacgttaaa aacatgatca ctggtgctgc tcaaatggac       300
ggcggtatct tagtagtatc tgctgctgac ggtccaatgc cacaaactcg tgaacacatt       360 ctttatcac gtaacgttgg tgtaccagca ttagtagtat tcttaaacaa agttgacatg       420
gttgacgatg aagaattatt agaattagta gaaatggaag ttcgtgactt attaagcgaa       480
tatgacttcc caggtgacga tgtacctgta atcgctggtt cagcattaaa agctttagaa       540
ggcgatgctc aatacgaaga aaaaatctta gaattaatgg aagctgtaga tacttacatt       600
ccaactccag aacgtgattc tgacaaacca ttcatgatgc cagttgagga cgtattctca       660
atcactggtc gtggtactgt tgctacaggc cgtgttgaac gtggtcaaat caaagttggt       720
gaagaagttg aaatcatcgg tttacatgac acatctaaaa caactgttac aggtgttgaa       780
atgttccgta aattattaga ctacgctgaa gctggtgaca cattggtgc attattacgt       840 ggtgttgctc gtgaagacgt acaacgtggt caagtattag ctgctcctgg ttcaattaca       900
ccacatactg aattcaaagc agaagtatac gtattatcaa aagacgaagg tggacgtcac       960
actccattct tctcaaacta tcgtccacaa ttctatttcc gtactactga cgtaactggt      1020
gttgttcact taccagaagg tactgaaatg gtaatgcctg tgataacgt tgaaatgaca      1080 gtagaattaa tcgctccaat cgcgattgaa gacggtactc gtttctcaat ccgtgaaggt      1140
ggacgtactg taggatcagg cgttgttact gaaatcatta aataa                     1185
```

<210> SEQ ID NO 23
<211> LENGTH: 812
<212> TYPE: DNA
<213> ORGANISM: Staphylococcus capitis
<220> FEATURE:
<221> NAME/KEY: misc_feature
<223> OTHER INFORMATION: tuf sequence

<400> SEQUENCE: 23

```
cggtatctta gtagtatctg ctgctgacgg tccaatgcca caaactcgtg aacacatctt        60
attatcacgt aacgttggtg taccagcatt agttgtattc ttaaacaaag ttgacatggt       120
agacgacgaa gaattattag aattagttga aatggaagtt cgtgacttat aagcgaata       180 tgacttccca ggtgatgatg tacctgtaat cgctggttca gcattaaaag ctttagaagg       240
cgatgctcaa tacgaagaaa aaatcttaga attaatgcaa gcagttgatg attacattcc       300
```

```
aactccagaa cgtgattctg acaaaccatt catgatgcca gttgaggacg tattctcaat    360
cactggtcgt ggtactgttg ctacaggccg tgttgaacgt ggtcaaatca agttggtga     420 agaagttgaa atcatcggta tccacgaaac ttctaaaaca actgttactg gtgtagaaat    480
gttccgtaaa ttattagact acgctgaagc tggtgacaac atcggtgctt tattacgtgg    540
tgttgctcgt gaagacgtac aacgtggtca agtattagct gctcctggtt caatcacacc    600
acacactaaa ttcaaagcgg aagtttacgt tttatctaaa gacgaaggtg acgtcacac     660 tccattcttc agtaactacc gcccacaatt ctatttccgt actactgacg taactggtgt    720
tgttaactta ccagaaggta ctgaaatggt tatgcctggc gacaacgttg aaatgacagt    780
tgaattaatc gctcctatcg ctattgaaga cg                                  812
```

<210> SEQ ID NO 24
<211> LENGTH: 812
<212> TYPE: DNA
<213> ORGANISM: Staphylococcus epidermidis
<220> FEATURE:
<221> NAME/KEY: misc_feature
<223> OTHER INFORMATION: tuf sequence

<400> SEQUENCE: 24

```
cggtatctta gttgtatctg ctgctgacgg tccaatgcca caaactcgtg aacacatctt    60
attatcacgt aacgttggtg taccagcatt agttgtattc ttaaacaaag ttgacatggt    120
agacgacgaa gaattattag aattagttga atggaagtt cgtgacttat taagcgaata     180
tgacttccca ggtgacgatg tacctgtaat cgctggttct gcattaaaag cattagaagg    240
cgatgctgaa tacgaacaaa aaatcttaga cttaatgcaa gcagttgatg attacattcc    300
aactccagaa cgtgattctg acaaaccatt catgatgcca gttgaggacg tattctcaat    360
cactggtcgt ggtactgttg ctacaggccg tgttgaacgt ggtcaaatca agttggtga     420 agaagttgaa atcatcggta tgcacgaaac ttctaaaaca actgttactg gtgtagaaat    480
gttccgtaaa ttattagact acgctgaagc tggtgacaac atcggtgctt tattacgtgg    540
tgttgcacgt gaagacgtac aacgtggtca agtattagct gctcctggtt ctattacacc    600
acacacaaaa ttcaaagctg aagtatacgt attatctaaa gatgaaggtg acgtcacac    660 tccattcttc actaactatc gcccacaatt ctatttccgt actactgacg taactggtgt    720
tgtaaactta ccagaaggta cagaaatggt tatgcctggc gacaacgttg aaatgacagt    780
tgaattaatc gctccaatcg ctatcgaaga cg                                  812
```

<210> SEQ ID NO 25
<211> LENGTH: 812
<212> TYPE: DNA
<213> ORGANISM: Staphylococcus haemolyticus
<220> FEATURE:
<221> NAME/KEY: misc_feature
<223> OTHER INFORMATION: tuf sequence

<400> SEQUENCE: 25

```
cggtatctta gtagtatctg ctgctgacgg tccaatgcca caaactcgtg aacacattct    60
tttatcacgt aacgttggtg taccagcatt agtagtattc ttaaataaag ttgacatggt    120
tgacgatgaa gaattattag aattagttga atggaagta cgtgacttat tatctgaata    180
cgacttccca ggtgacgatg tacctgtaat cgctggttca gcattaaaag ctttagaagg    240
cgatgctcaa tacgaagaaa aaatcttaga attaatgcaa gcagttgatg actacattcc    300
aactccagaa cgtgattctg acaaaccatt catgatgcca gttgaggacg tattctcaat    360
```

```
cactggtcgt ggtactgttg ctacaggccg tgttgaacgt gggcaaatca aagttggtga    420
agaagttgaa atcattggta tccatgcact tctaaaaca actgttactg gtgtagaaat     480
gttccgtaaa ttattagact acgctgaagc tggtgacaac atcggtgcat tattacgtgg    540
tgttgctcgt gaagacgtac aacgtggtca agtattagct gctccaggtt caatcacacc    600
tcacacaaaa tttaaagcag acgtatacgt tttatctaaa gacgaaggtg acgtcacac    660 tccattcttc acaaactatc gtccacaatt ctatttccgt actactgacg taactggtgt    720
tgttaactta ccagaaggta ctgaaatggt tatgcctggc gacaacgttg aaatgacagt    780
agaattaatc gctcctatcg cgattgaaga cg                                  812

<210> SEQ ID NO 26
<211> LENGTH: 812
<212> TYPE: DNA
<213> ORGANISM: Staphylococcus hominis
<220> FEATURE:
<221> NAME/KEY: misc_feature
<223> OTHER INFORMATION: tuf sequence

<400> SEQUENCE: 26
cgctatctta gtagtatctg ctgctgatgg tccaatgcca caaactcgtg aacacattct     60
tttatcacgt aacgttggtg taccagcatt agtagtattc ttaaacaaag ttgacatggt    120
tgacgatgaa gaattattag aattagttga atggaagta cgtgacttat tatctgaata    180
cgacttccca ggtgacgacg tacctgtaat cgctggttca gctttaaaag ctttagaagg    240
cgatgctcaa tacgaagaaa aaatcttaga attaatgcaa gcagttgatg attatattcc    300
aactccagaa cgtgactctg ataaaccatt catgatgcca gttgaggacg tattctcaat    360
cactggtcgt ggtactgttg ctacaggccg tgttgaacgt ggtcaaatca aagttggtga    420
agaagttgaa attattggta tcaaagaaac ttctaaaaca actgttactg gtgtagaaat    480
gttccgtaaa ttattagact acgctgaagc tggtgacaac atcggtgctt tattacgtgg    540
tgttgctcgt gaagatgtac aacgtggtca agtattagct gctccaggtt caattacacc    600
tcacacaaaa ttcaaagcag acgtatacgt tttatcaaaa gatgaaggtg acgtcatac    660 tccattcttc tctaactatc gtccacaatt ctatttccgt actactgacg taactggtgt    720
tgttaactta ccagaaggta ctgaaatggt aatgcctggt gacaacgttg aaatgacagt    780
agaattaatc gctcctatcg cgattgaaga cg                                  812

<210> SEQ ID NO 27
<211> LENGTH: 812
<212> TYPE: DNA
<213> ORGANISM: Staphylococcus lugdunensis
<220> FEATURE:
<221> NAME/KEY: misc_feature
<223> OTHER INFORMATION: tuf sequence

<400> SEQUENCE: 27
cggtatctta gtagtttctg ctgcagatgg tccaatgcca caaactcgtg aacacattct     60
tttatcacgt aacgttggtg tgccagcatt agtagtattc ttaaacaaag ttgacatggt    120
tgacgatgaa gaattattag aattagtaga atggaagtt cgtgatttat taactgaata    180
tgacttccca ggtgacgatg tgcctgtaat cgctggttca gcattaaaag ctttagaagg    240
cgacgaaaaa tacgaagcta aaatcttaga attaatggat gcagttgata actacattcc    300
aactccagaa cgtgactctg acaaaccatt catgatgcca gttgaggacg tattctcaat    360
```

| | |
|---|---|
| cactggtcgt ggtactgttg ctacaggccg tgttgaacgt ggtcaaatca aagtcggtga | 420 |
| agaagttgaa attattggta tccacgatac tactaaaaca actgttactg gtgtagaaat | 480 |
| gttccgtaaa ttattagact acgctgaagc tggtgacaac atcggtgcgt tattacgtgg | 540 |
| tgttgctcgt gaagatgtac aacgtggaca agtattagct gctccaggtt caattacacc | 600 |
| tcacactaaa tttaaagctg acgtatatgt tttatctaaa gatgaaggtg acgtcatac | 660 |
| accattcttc tcaaactacc gcccacaatt ctatttccgt actacagacg taactggtgt | 720 |
| tgttaactta ccagaaggta cagaaatggt tatgcctggc gacaacgttg aaatgacagt | 780 |
| tgaattaatc gctccaatcg ctatcgaaga cg | 812 |

```
<210> SEQ ID NO 28
<211> LENGTH: 753
<212> TYPE: DNA
<213> ORGANISM: Staphylococcus simulans
<220> FEATURE:
<221> NAME/KEY: misc_feature
<223> OTHER INFORMATION: tuf sequence

<400> SEQUENCE: 28
```

| | |
|---|---|
| cggcgcagat ggacggcggt atcttagtag tatctgctgc agatggtcca atgccacaaa | 60 |
| ctcgtgaaca catcttatta tcacgtaacg ttggtgtacc agctttagtt gtattcttaa | 120 |
| acaaagctga catggttgac gacgaagaat tattagaatt agttgaaatg gaagttcgtg | 180 |
| acttattatc tgaatacgac ttccctggtg acgatgtacc agttatcgtt ggttctgcat | 240 |
| taaaagcttt agaaggcgac ccagaatacg aacaaaaaat cttagactta atgcaagctg | 300 |
| tagatgacta catcccaact ccagaacgtg actctgataa accattcatg atgccagttg | 360 |
| aggacgtatt ctcaatcact ggtcgtggta ctgtagcaac aggccgtgtt gaacgtggtc | 420 |
| aaatcaaagt cggtgaagaa gttgaaatca tcggtatcac tgaagaaagc aagaaaacaa | 480 |
| cagttacagg tgtagaaatg ttccgtaaat tattagacta cgctgaagct ggtgacaaca | 540 |
| tcggtgcttt attacgtggt gttgcacgtg aagacgtaca acgtggacaa gtattagcag | 600 |
| ctccggctc tattactcca cacacaaaat tcaaagctga tgtttacgtt ttatctaaag | 660 |
| aagaaggtgg acgtcatact ccattcttca ctaactaccg cccacaattc tacttccgta | 720 |
| ctactgacgt aactggcgtt gttcacctac cag | 753 |

```
<210> SEQ ID NO 29
<211> LENGTH: 812
<212> TYPE: DNA
<213> ORGANISM: Staphylococcus warneri
<220> FEATURE:
<221> NAME/KEY: misc_feature
<223> OTHER INFORMATION: tuf sequence

<400> SEQUENCE: 29
```

| | |
|---|---|
| cggtatctta gttgtatctg cagctgatgg tccaatgcca caaactcgtg aacacattct | 60 |
| tttatcacgt aacgttggtg taccagcttt agttgtattc ttaaacaaag ttgatatggt | 120 |
| agacgacgaa gaattattag aattagtaga aatggaagtt cgtgactta tatctgaata | 180 |
| tgacttccca ggtgacgacg tacctgtaat cgctggttca gcattaaaag ctttagaagg | 240 |
| cgacgaaaaa tacgaagaaa aaatcttaga attaatgcaa gcagttgatg actacattcc | 300 |
| aactccagaa cgtgattctg acaaaccatt catgatgcca gttgaggacg tattctcaat | 360 |
| cactggtcgt ggtactgttg ctacaggccg tgttgaacgt ggtcaaatca aagttggtga | 420 |
| agaagttgaa atcatcggtt tacatgacac ttctaaaaca actgttactg gtgtagaaat | 480 |

```
gttccgtaag ttattagact acgctgaagc tggtgacaac atcggtgctt tattacgtgg      540
tgttgctcgt gaagacgtac aacgtggtca agtattagct gctcctggtt caattacacc      600
acatacaaaa ttcaaagcgg aagtttacgt tttatctaaa gacgaaggtg gacgtcacac      660
tccattcttc agtaactacc gcccacaatt ctatttccgt actactgacg taactggcgt      720
tgttcaatta ccagaaggta ctgaaatggt tatgcctggt gataacgttg aaatgacagt      780
agaattaatc gctcctatcg cgattgaaga cg                                    812
```

<210> SEQ ID NO 30
<211> LENGTH: 2007
<212> TYPE: DNA
<213> ORGANISM: Staphylococcus aureus
<220> FEATURE:
<221> NAME/KEY: misc_feature
<223> OTHER INFORMATION: mecA sequence

<400> SEQUENCE: 30

```
ttattcatct atatcgtatt ttttattacc gttctcatat agctcatcat acactttacc       60
tgagattttg gcattgtagc tagccattcc tttatcttgt acatctttaa cattaatagc      120
catcatcatg tttggattat ctttatcata tgatataaac cacccaattt gtctgccagt      180
ttctccttgt ttcattttga gttctgcagt accggatttg ccaattaagt ttgcataaga      240
tctataaata tcttctttat gtgttttatt tacgacttgt tgcataccat cagttaatag      300
attgatattt tctttggaaa taatattttt cttccaaact ttgttttcg tgtcttttaa       360 taagtgaggt gcgttaatat tgccattatt ttctaatgcg ctatagattg aaaggatctg      420
tactgggtta atcagtattt caccttgtcc gtaacctgaa tcagctaata atatttcatt      480
atctaaattt ttgttttgaaa tttgagcatt ataaaatgga taatcacttg gtatatcttc     540
accaacacct agttttttca tgccttttc aaatttctta ctgcctaatt cgagtgctac      600
tctagcaaag aaaatgttat ctgatgattc tattgcttgt tttaagtcga attaccatt      660 taccacttca tatcttgtaa cgttgtaacc accccaagat ttatctttt gccaaccttt       720 accatcgatt ttataacttg ttttatcgtc taatgtttg ttatttaacc caatcattgc       780
tgttaatatt ttttgagttg aacctggtga agttgtaatc tggaacttgt tgagcagagg      840 ttcttttta tcttcggtta atttattata ttccttcgtta ctcatgccat acataaatgg     900
atagacgtca tatgaaggtg tgcttacaag tgctaataat tcacctgttt gagggtggat      960
agcagtacct gagccataat catttttcat gttgttataa atactctttt gaactttagc     1020
atcaatagtt agttgaatat ctttgccatc tttttttcttt ttctctatta atgtatgtgc    1080
gattgtattg ctattatcgt caacgattgt gacacgatag ccatcttcat gttggagctt     1140
tttatcgtaa agtttttcga gtccctttt accataact gcatcatctt tatagccttt       1200
atattctttt tgttttaatt cttcagagtt aatgggacca acataaccta atagatgtga    1260
agtcgctttt cctagaggat agttacgact ttctgtttca ttagttgtaa gatgaaattt     1320
ttttgcgaaa tcacttaaat attcatccat tttttaacg ttttaagtg gaacgaaggt      1380 atcatcttgt acccaattt gatccatttg ttgtttgata tagtcttcag aaatacttag     1440
ttctttagcg attgctttat aatctttttt agatacattc tttggaacga tgcctatctc     1500
atatgctgtt cctgtattgg ccaattccac attgttccgg tctaaaattt taccacgttc     1560
tgattttaaa ttttcaatat gtatgctttg gtctttctgc attcctggaa taatgacgct    1620
atgatcccaa tctaacttcc acataccatc ttctttaaca aaattaaatt gaacgttgcg     1680
```

-continued

```
atcaatgtta ccgtagtttg ttttaatttt atattgagca tctactcgtt ttttattttt    1740 agatacttt  tttattttac gatcctgaat gtttatatct ttaacgccta aactattata    1800
tatttttatc ggacgttcag tcatttctac ttcaccatta tcgcttttag aaatataact    1860
gctatcttta taaacttgtt tgaaattttt atcttcaatt gcatcaatag tattattaat    1920
ttctttatct tttgaagcat aaaaatatat accaaacccg acaactacaa ctattaaaat    1980
aagtggaaca atttttatct ttttcat                                        2007
```

METHODS, KITS, AND COMPOSITIONS FOR DETECTION OF MRSA

CROSS-REFERENCE TO RELATED APPLICATIONS

This application claims the priority of U.S. provisional applications entitled METHODS, KITS, AND COMPOSITIONS USEFUL IN THE DETECTION OF MRSA, with application No. 61/315,664, filed on Mar. 19, 2010; and U.S. provisional applications entitled METHODS, KITS AND COMPOSITIONS FOR DETECTION OF MRSA, with application No. 61/432,511, filed on Jan. 13, 2011, both of which are hereby incorporated by reference in their entirety.

This invention was made with government support under AI066581 awarded by the National Institutes of Health. The government has certain rights in this invention.

FIELD OF THE INVENTION

The present invention generally provides compositions and methods to determine whether there is presence of methicillin-resistant *Staphylococcus aureus* (MRSA) in a given sample. More particularly, the present invention provides assays based on identified gene sequences, primers and probes designed accordingly to detect the presence of MRSA. The present invention further comprises assays useful to identify and differentiate MRSA, MSSA, MRSE, MSSE, MRCNS and MSCNS in samples.

BACKGROUND OF THE INVENTION

Methicillin-resistant *Staphylococcus aureus* (MRSA) has become one of the most dangerous infectious agents in the U.S. and elsewhere, with a higher mortality rate than HIV-AIDS. MRSA is a strain of *Staphylococcus aureus* (*S. aureus*) bacteria, a common type of bacteria that may live on the skin and in the nasal passages of healthy people. MRSA does not respond to some of the antibiotics generally used to treat *staphylococcus* and other bacterial infections.

Healthcare-associated MRSA (HA-MRSA) infections occur in people who are or have recently been in a hospital or other health-care facility. Many people may be at risk of MRSA infection due to receiving healthcare services in an environment where the MRSA bacteria are colonized on surfaces, healthcare workers, the patient or other patients. Community-associated MRSA (CA-MRSA) infections occur in otherwise healthy people who have not recently been in the hospital. In fact, MRSA has become a primary cause of skin and soft tissue infections among persons without extensive exposure to healthcare settings, and the outbreaks have occurred in athletic team facilities, correctional facilities, and military basic training camps.

In addition to methicillin-sensitive *S. aureus* (MSSA) and methicillin-resistant *S. aureus* (MRSA) strains, there are CNS, or CoNS, (coagulase-negative staphylococci) species, close relatives of the bacterium *Staphylococcus aureus*, commonly found in humans. Many strains of CNS are also resistant to methicillin (MRCNS) containing a similar SCC-mec gene cassette mechanism as MRSA. Specifically, methicillin-resistant *S. epidermidis* (MRSE) is the species in the CNS complex of species most commonly seen among MRCNS carriers. Among immunocompromised patients, MRCNS, especially MRSE, can lead to infections and is a common cause of wound, blood and respiratory infections. MRSE can cause severe infections in immune-suppressed patients and those with central venous catheters.

Interventions for MRSA colonization through decolonization, isolation procedures, or restrictions in occupational activities among clinicians and patients would be more effective if there was a way to rapidly identify patients among healthcare workers who are colonized with MRSA. However, current identification systems are based on outdated, cumbersome, and time consuming technologies, such as culturing, and are focused only on MRSA. Therefore, there is an ongoing need for technologies that enable positive identification and differentiation of MRSA, MSSA, MRCNS and MSCNS using more rapid and informative tests with a high level of accuracy for both screening for colonization and diagnosis of infections.

SUMMARY OF THE INVENTION

Briefly, therefore, one aspect of the present invention provides a multiplex assay for identifying and differentiating MRSA, MSSA, MRSE, MSSE, MRCNS and MSCNS in a sample. The multiplex assay comprises more than one assay chosen from nuc-SA assay, femA-SA assay, femA-Se assay, tuf-Sa assay, tuf-CNS assay, and mecA assay.

Another aspect of the invention encompasses a multiplex assay for identifying and differentiating MRSA, MSSA, MRSE, and MSSE in a sample, and the multiplex assay comprises femA-Se assay; mecA assay; and at least one assay chosen from the nuc-Sa assay and femA-S a assay.

Another aspect of the invention provides a multiplex assay for identifying and differentiating MRSA, MSSA, MRSE, MSSE, MRCNS and MSCNS in a sample, the multiplex assay comprising mecA assay and two assays chosen from femA-Se assay, tuf-Sa assay, and tuf-CNS assay.

A further aspect of the invention encompasses a method for identifying and differentiating MRSA, MSSA, MRSE, MSSE, MRCNS and MSCNS in a sample. The method comprises receiving a sample; screening the sample by carrying out at least one assay chosen from nuc-Sa assay, femA-Sa assay, femA-Se assay, tuf-Sa assay, tuf-CNS assay, and mecA assay, which respectively analyze the presence or absence of nuc-*S. aureus* gene, the femA-*S. aureus* gene, the femA-*S. epidermis* gene, the tuf-*S. aureus* gene, the tuf-CNS gene and the mecA gene; and identifying the bacteria contained in the sample as MRSA, MSSA, MRSE, MSSE, MRCNS or MSCNS based on the analysis of each chosen assay.

Yet another aspect of the invention provides a kit for identifying and differentiating MRSA, MSSA, MRSE, MSSE, MRCNS and MSCNS in a sample through a multiplex assay. The kit comprises one or more primer sets and probes for assays chosen from nuc-Sa assay, femA-Sa assay, femA-Se assay, tuf-Sa assay, tuf-CNS assay and mecA assay.

Other aspects and iterations of the invention are described in more detail below.

DETAILED DESCRIPTION OF THE INVENTION

Figure 1:
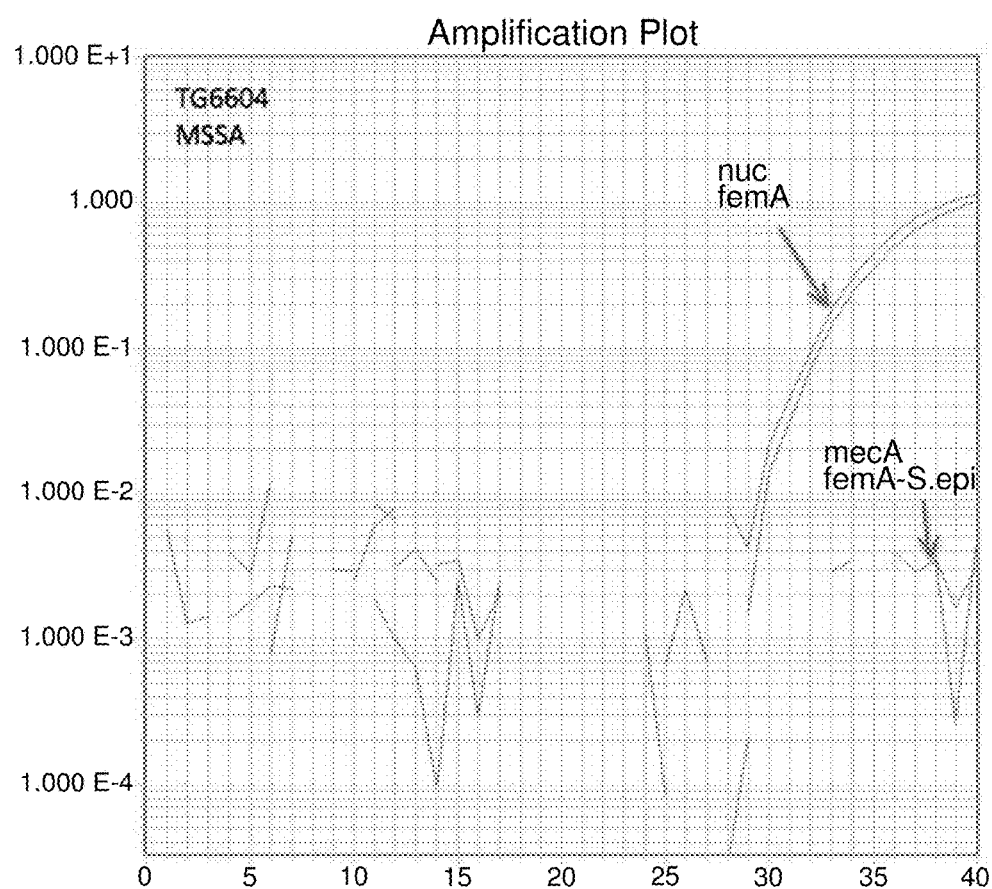
FIG. 1 depicts the results of four real-time PCR assays comprising nuc-Sa, femA-SA (same as femA-Sa, same below), femA-Sepi (same as fem-Se, same below) and mecA assays; the multiplex assay was used to analyze the throat swab sample designated TG6604.

The present invention discloses assays, methods and kits designed to identify and differentiate among MSSA, MRSA, MRCNS and MSCNS, including the MRSE and MSSE of the CNS species, in mixed specimens using a multiplex assay comprising a combination of variable individual assays or using individual assays depending on the application.

(I) Detection of MRSA and Other Species or Strains (a) Molecules Identifying and Differentiating MRSA and Other Species or Strains In addition to methicillin-sensitive *S. aureus* (MSSA) and methicillin-resistant *S. aureus* (MRSA.), there are CNS, or CoNS, (coagulase-negative staphylococci) commonly found in humans, which are close relatives of *Staphylococcus aureus*. Many CNS are also resistant to methicillin (MRCNS) carrying a similar SCCmec gene cassette mechanism as MRSA. Among the CNS species, the exemplary examples include: *S. capitis, S. epidermidis, S. haemolyticus, S. hominis, S. lugdunensis, S. saprophyticus, S. simulans,* and *S. warneri*. Specifically, methicillin-resistant *S. epidermidis* (MRSE) is the CNS species most commonly seen among MRCNS carriers. Among immunocompromised patients, MRCNS, especially MRSE, can lead to infections and is common cause of wound, blood, medical device and respiratory infections.

A subject may display signs or symptoms of bacterial infection, including infection with MRSA. However, these signs or symptoms are not reliable in diagnosing MRSA, MSSA, MRCNS or MRCNS. In comparison, utilizing species or strain specific nucleic acid sequences, alleles of those sequences, or biomarkers derived from transcriptional or translational products of the species or strain specific nucleic acid sequences and their alleles for identifying and differentiating MRSA, MSSA, MRSE, MSSE, MRCNS and MSCNS is much more rapid, accurate and informative.

(i) Species or Strain Specific Nucleic Acid Sequences

Species or strain specific sequences are sequences unique to the species or strain, that is, not shared by other previously characterized species or strains. A probe or primer containing a sequence complementary to a sequence specific to a *S. aureus* species, *S. epidermidis*, CNS, or strains thereof will typically not hybridize to the corresponding portion of the genome of other species or strains under stringent conditions. When a particular species or strain sequence is identified, probes or primers may be designed based on any part of the sequence. The probes or primers may also be the entirety of the sequence. The primers or probes designed according to particular species or strain sequence may also be represented in degenerate form, or comprising chemically modified nucleic acids, or any other components that facilitate the identification of the identifying sequence of a strain or species. The concept of a sequence identified to be specific to a species or strain further encompasses nucleic acid sequences that are less than 100% identical to the specific sequence, but are still capable of specifically detecting the species or strain. Note that in a nucleic acid sequence, T or U may be used interchangeably depending on whether the nucleic acid is DNA or RNA. A sequence having less than 60% 70%, 80%, 90%, 95%, 99% or 100% identity to the identifying sequence may still be encompassed by the invention if it is able of binding to its complimentary sequence and/or facilitating nucleic acid amplification of a desired target sequence. The primers or probes designed according to particular species or strain sequence may also be represented in degenerate form, or comprising chemically modified nucleic acids, or any other components that facilitate the identification of the identifying sequence of a strain or species.

Identifying the species or strain specific sequences and developing the probes or primers to detect the presence of those sequences to identify and differentiate MRSA, MSSA, MRCNS or MRCNS are disclosed herein. One aspect of the present invention discloses that nuc-*S. aureus* gene can be used to specifically detect *S. aureus*. Another aspect of the present invention discloses that femA-*S. aureus* gene can also be used to specifically detect *S. aureus*. Another aspect of the present invention discloses that differences in the tuf genes in *S. aureus* and CNS can be used to differentiate the two close relatives. Yet another aspect of the present invention discloses that the femA-*S. epi* gene can be used to specifically detect *Staphylococcus epidermidis*, that is, MSSE or MRSE. A further aspect of the present invention discloses that the mecA gene can be used to specifically determine methicillin/penicillin resistance in *S. aureus* and CNS.

(ii) Alleles of Species or Strain Specific Nucleic Acids

Identifying alleles to a sequence specific to a *S. aureus* species, *S. epidermidis*, CNS, or strains thereof, is another aspect of this invention. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spacial expression specificity. The presence or absence of an allele may be detected through the use of any process known in the art, including using primers and probes designed accordingly for PCR, sequencing, hybridization analyses. An allele may also be called a mutation or a mutant. An allele may be compared to another allele that may be termed a wild type form of an allele. In some cases, the wild type allele is more common than the mutant.

One aspect of the present invention provides that nuc-*S. aureus* gene alleles may be used to specifically detect *S. aureus*. Another aspect of the present invention provides that femA-*S. aureus* gene alleles may also be used to specifically detect *S. aureus*. Another aspect of the present invention provides that the differences in the tuf genes in *S. aureus* and CNS may be used to differentiate the two close relatives. Yet another aspect of the present invention provides that the femA-*S. epi* gene alleles may be used to specifically detect *Staphylococcus epidermidis*, that is, MSSE or MRSE. A further aspect of the present invention provides that the mecA gene allele can be used to specifically determine methicillin/penicillin resistance in *S. aureus* and CNS. The present invention also provides additional DNA sequences that may be used to develop MRSA, MSSA, MRSE, MSSE, MRCNS and MSCNS identification and differentiation assays (see Example 5 and SEQ ID NO. 19-30)

(iii) Biomarkers as Indications of the Presence of Specific Species or Strain

Molecules, including but not limited to small RNAs, peptides and proteins, derived from transcription or translation process of the MRSA, MSSA, MRSE, MSSE, MRCNS, MSCNS or other species or strain specific nucleic acid sequences and alleles thereof may serve as biomarkers indicating the presence of a particular species or strain. Some molecules that are produced by immune system to defend against MRSA, MSSA, MRSE, MSSE, MRCNS, or MSCNS, for example _____, may also serve as biomarkers. Methods of detecting an allele generally involve assessing the expression of material created from a genomic DNA template such as an RNA or protein molecule. Such expression may be assessed by any of a number of methods used currently in the art and yet to be developed.

Once strain specific genes, alleles thereof, or other nucleic acid based biomarkers thereof, are identified, primers and probes may be designed to screen samples to specifically and selectively detect the presence or absence of these genes, alleles or biomarkers, and therefore, a particular species or strain of *Staphylococcus* may be determined through various methods including PCR-based methods such as real-time PCR, quantitative PCR, quantitative real time PCR; allele specific ligation; comparative genomic hybridization; sequencing; and other methods known in the art. In one exemplary example, the tuf gene of the CNS species was aligned in order to design the primers used in the assay to detect CNS. The working mechanism of primers in RT-PCR/PCR is known in the art. One aspect of the invention provides multiplex RT-PCR assays combining various numbers of assays that comprise specific primer sets and probes depending on the application to differentiate between MRSA, MSSA, MRSE, MSSE, MRCNS, and MSCNS in mixed specimens.

As to probes, they may be used for single probe analysis or multiplex probe/primer combined RT-PCR/PCR analysis. Oligonucleotide probes complimentary to a selected sequence within the target sequence may be designed. In one exemplary example, oligonucleotide probes facilitating RT-PCR/PCR product detection are complimentary to a selected sequence within the target sequence downstream from either the upstream or downstream primer. Therefore, these probes hybridize to an internal sequence of the amplified fragment of a targeted sequence.

The concept of oligonucleotides includes any DNA or RNA molecule of two or more nucleotides, whether from a natural source, artificially synthesized, or produced through the use of recombinant DNA technology. A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide sequence. The length of the oligonucleotide depends on how the oligonucleotide will be used. One skilled in the art would understand the approximate length of oligonucleotide necessary in any given method. Depending on the method, an oligonucleotide may be 0 to 1000 bases in length. In other aspects, it may be 5 to 500 bases in length, 5 to 100 bases in length, 5 to 50 bases in length, or 10 to 30 bases in length. The primers or probes designed according to a particular species or strain sequence may also be represented in degenerate form, or comprising chemically modified nucleic acids, or any other components that facilitate the identification of the identifying sequence of a strain or species. An oligonucleotide may be in any physical formulation including as a solid (including crystal salts as necessary,) or it may be in a solution such as in a buffered solution.

(b) Samples that May Contain MRSA and Other Species or Strains

Samples often come with a mixture of bacterium species. In addition to MSSA and MRSA, there are CNS, or CoNS. Among the CNS species, MRSE is the strain most commonly seen among MRCNS carriers. The present invention discloses multiplex assays utilizing primer sets and/or probes, methods and kits designed to differentiate among MSSA, MRSA, MRCNS and MSCNS, including the MRSE and MSSE of the CNS species, in a sample using a multiplex assay comprising a combination of variable individual assays depending on the application.

A sample subjected to the assays, methods or kits disclosed herein may or may not be suspected of containing a nucleic acid from a bacterium of interest. Nucleic acids may include but need not be limited to RNA, cDNA, tRNA, mitochondrial DNA, plasmid DNA, siRNA, genomic DNA, or any other naturally occurring or artificial nucleic acid molecule originating from a bacterium. Samples may be suspected of containing a bacterium if they are derived from a subject displaying symptoms of a bacterial infection, or from an environmental sample from an area in which a bacterium is thought to be endemic, or from a subject recently present in a hospital or other environment found to contain MRSA or MRSE. A subject may display signs or symptoms of MRSA infection, which include red, swollen and painful areas on the skin, drainage of pus or other fluids from the site, fever, skin abscesses, warmth around the infected area, chest pain, chills, cough, fatigue, malaise, headache, muscle ache, rash, and shortness of breath.

A sample may be derived from anywhere that a bacterium or any part of a bacterium may be found, including but not limited to soil, air, water, solid surfaces (whether natural or artificial,) culture media, foodstuffs, devices, including devices used in medical procedures and/or bodily embellishment procedures (such as tattoo needles or body piercing needles). Additionally, a sample may be derived from a subject, or from agricultural, environmental, or any and all other sources.

A subject may be any organism that may be infected by a bacterium, such as plants; animals, including but not limited to humans, companion animals such as dogs, cats, birds, or small mammals, livestock animals such as cattle, pigs, sheep, poultry and any other domesticated or wild animal. Samples derived from subjects include but are not limited to a collection of nucleic acids in all forms, biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF), cerebrospinal fluid, semen, amniotic fluid, lacrimal fluid, stool, urine, hair, or any other source in which a bacterium, or any part of a bacterium might be present.

Samples may be collected by any and all methods now known or yet to be disclosed, including swiping or swabbing an area or orifice, removal of a piece of tissue as in a biopsy, any method known to collect bodily fluids, wiping down a surface, collecting a sample of liquid, collecting an air sample or any other method that may be used to collect bacteria in such a way as to preserve biological material such as DNA, RNA or protein for analysis.

(c) Preferred Embodiments

As shown in Table A, in one preferred embodiment of the present invention, primer set 1, represented by SEQ ID NO. 1 and 2, is selective for *S. aureus*-specific nucleic sequence carrying nuc gene, so that *S. aureus*, CNS and other species can be differentiated.

In one preferred embodiment, primer set 2 represented, by SEQ ID NO. 4 and 5, is selective for *S. aureus*-specific nucleic sequence carrying femA-*S. aureus* gene, so that *S. aureus*, CNS and other species can be differentiated.

In one preferred embodiment, primer set 3, represented by SEQ ID NO. 7 and 8, is selective for *S. epi*-specific nucleic sequence carrying femA-*S. epi* gene, so that *S. epidermis* and other *Staphylocossus* species can be differentiated.

In one preferred embodiment, primer set 4, represented by SEQ ID NO. 10 and 11, is selective for *S. aureus*-specific nucleic sequence carrying tuf-*S. aureus* gene, so that *S. aureus* can be detected.

In one preferred embodiment, primer set 5, represented by SEQ ID NO. 13 and 14, is selective for CNS-specific nucleic sequence carrying tuf-CNS gene, so that CNS can be detected.

In yet another preferred embodiment, primer set 6, represented by SEQ ID NO. 16 and 17, is selective for methicillin or penicillin resistance, a phenotype determined by the presence or absence of the nucleic sequence carrying mecA gene, so that methicillin and penicillin resistance phenotypes can be differentiated.

In still another preferred embodiment, probe 1, represented by SEQ ID NO. 3, is selective for *S. aureus*-specific nucleic sequence carrying nuc gene, so that *S. aureus*, CNS and other species can be differentiated.

In one preferred embodiment, probe 2, represented by SEQ ID NO. 6, is selective for *S. aureus*-specific nucleic sequence carrying femA-*S. aureus* gene, so that *S. aureus*, CNS and other species can be differentiated.

In one preferred embodiment, probe 3, represented by SEQ ID NO. 9, is selective for *S. epi*-specific nucleic sequence carrying femA-*S. epi* gene, so that *S. epidermidis* from other *Staphylocossus* species can be differentiated.

In one preferred embodiment, probe 4, represented by SEQ ID NO. 12, is selective for *S. aureus*-specific nucleic sequence carrying tuf-*S. aureus* gene, so that *S. aureus* can be detected.

In yet another preferred embodiment, probe 5, represented by SEQ ID NO. 15, is selective for CNS-specific nucleic sequence carrying tuf-CNS gene, so that CNS can be detected.

In still another preferred embodiment, probe 6, represented by SEQ ID NO. 18, is selective for methicillin or penicillin resistance, a phenotype determined by the presence or absence of the nucleic sequence carrying mecA gene, so that methicillin and penicillin resistance phenotypes can be differentiated.

The oligonucleotides for the primers and probes may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task.

TABLE A

Assays, Primers and Probes

| Assay No. | Primer/Probe No. | SEQ ID NO. | Description |
|---|---|---|---|
| Assay 1: nuc-Sa assay | Primer Set 1 | 1 | Identify and differentiate |
| | | 2 | *S. aureus* and other |
| | Probe 1 | 3 | species |
| Assay 2: femA-Sa assay | Primer Set 2 | 4 | Identify and differentiate |
| | | 5 | *S. aureus* and other |
| | Probe 2 | 6 | species |
| Assay 3: femA-Se assay | Primer Set 3 | 7 | Identify and differentiate |
| | | 8 | *S. epidermis* from |
| | Probe 3 | 9 | other *Staphylocossus* species |
| Assay 4: tuf-Sa assay | Primer Set 4 | 10 | Identify *S. aureus* |
| | | 11 | |
| | Probe 4 | 12 | |
| Assay 5: tuf-CNS assay | Primer Set 5 | 13 | Identify CNS |
| | | 14 | |
| | Probe 5 | 15 | |
| Assay 6: mecA assay | Primer Set 6 | 16 | Identify and differentiate |
| | | 17 | methicillin and penicillin |
| | Probe 6 | 18 | resistance phenotypes |

(II) Methods for Detecting MRSA and Other Species or Strains

Methods that can be used to identify strain specific nucleic acids, alleles of strain specific nucleic acids, and biomarkers derived from transcriptional and translational products of the strain specific nucleic acids and the alleles thereof, include PCR, RT-PCR, hybridization, sequencing and any combination of the above methods.

A nucleic acid may be added to a sample by any of a number of methods, including manual methods, mechanical methods, or any combination thereof. The presence of the allele may be signified by any of a number of methods, including amplification of a specific nucleic acid sequence, sequencing of a native or amplified nucleic acid, or the detection of a label either bound to or released from the nucleic acid. Addition of the nucleic acid to the sample also encompasses addition of the nucleic acid to a sample in which the target allele to which the nucleic acid has specificity is absent.

(a) PCR

Nucleic acids may be selectively and specifically amplified from a template nucleic acid contained in a sample. In some nucleic amplification methods, the copies are generated exponentially. Non-limiting nucleic acid amplification methods known in the art include: the polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with Klenow or any other RNA polymerase, or any other method by which copies of a desired sequence are generated.

Polymerase Chain Reaction (PCR) is a highly efficient method of amplifying template DNA, generally involving the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage, (typically 80-100° C.) an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complimentary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethyl-amino-phenylazo)benzoic acid ("Dabcyl"); 4-(4'-dimethyl-amino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping.

Examples of such dyes include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ-.PCR facilitating the reading of the target amplification.

Either primers or primers along with probes, as described above, will allow a quantification of the amount of specific template DNA present in the initial sample. In addition, RNA may be detected by PCR analysis by first creating a DNA template from RNA through a reverse transcriptase enzyme. In some aspects of the invention, the allele may be detected by quantitative PCR analysis facilitating genotyping analysis of the samples.

As an exemplary example, the use of dual-labeled oligonucleotide probes in PCR reactions is disclosed in U.S. Pat. No. 5,716,784 to DiCesare. In the PCR step of the multiplex RT-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Apparatus suitable for detection include Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex RT-PCR/PCR can also be performed in other real-time PCR systems with multiplexing capabilities.

In multiplex PCR assays, relative quantification is often used to determine the changes in steady-state mRNA levels of a gene across multiple samples, and describe the level of mRNA in reference to the levels of an internal control RNA (reference). The control RNA may be co-amplified in the same tube in a multiplex assay or may be amplified in a separate tube. Generally, the control RNA may be a house keeping gene, or gene with constitutive expression, or a standard with known concentration. In relative quantification, however, it does not require standards with known concentrations and the reference can be any transcript, as long as its sequence is known. Relative quantification is based on the expression levels of a target gene versus one or more reference gene(s), and in many experiments, it is adequate for investigating physiological changes in gene expression levels. To calculate the expression of a target gene in relation to an adequate reference gene, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in RT-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the RT-PCR reaction.

Alternatively, the Cp value may be utilized. Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

(b) Hybridization

In addition to PCR, genotyping analysis may also be performed using a probe that is capable of hybridizing to a nucleic acid sequence of interest. Probes may include nucleic acids, oligonucleotides (DNA or RNA), proteins, protein complexes, conjugates, natural ligands, small molecules, nanoparticles, or any combination of molecules that includes one or more of the above, or any other molecular entity capable of specific binding to any allele, whether such molecular entity exists now or is yet to be disclosed. In one aspect of the invention, the probe comprises an oligonucleotide. The description of oligonucleotide is in Section I (ii).

Methods of detecting a gene or an allele generally involve assessing their expression level through their transcriptional or translational products such as a RNA or protein molecule. The expression of a gene or an allele may be assessed by any of a number of methods used currently in the art and yet to be developed. Examples include any nucleic acid detection method, including the following nonlimiting examples, microarray analysis, RNA in situ hybridization, RNAse protection assay, Northern blot. Other examples include any process of detecting expression that uses an antibody including the following nonlimiting examples, flow cytometry, immunohistochemistry, ELISA, Western blot, Northwestern blot, and immunoaffinity chromatograpy. Antibodies may be monoclonal, polyclonal, or any antibody fragment, for example, Fab, F(ab)$_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

In some aspects of the invention, the presence of an allele may be established by binding to probes on a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample, and consequently, the presence of the allele in the sample.

In allele-specific hybridization, oligonucleotide sequences representing all possible variations at a polymorphic site are included on a chip. The chip and sample are subject to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A nucleic acid probe may be affixed to a substrate. Alternatively, a sample may be affixed to the substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, either singly or in the presence of one or more additional probes or samples as is exemplified in a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A nucleic acid probe may include a label. A label may be any substance capable of aiding a machine, detector, sensor, device, or enhanced or unenhanced human eye from differentiating a labeled composition from an unlabeled composition. Examples of labels include, but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof, or any other compound that may be differentially detected. The label may also include one or more fluorescent dyes optimized for use in genotyping. Examples of such dyes include, but are not limited to: dR110, 5-FAM, 6FAM, dR6G, JOE, HEX, VIC, TET, dTAMRA, TAMRA, NED, dROX, PET, BHQ+, Gold540, and LIZ.

(c) Sequencing

Methods of detecting the presence of a gene or an allele further include, but are not limited to, any form of DNA sequencing including Sanger, next generation sequencing, pyrosequencing, SOLID sequencing, massively parallel sequencing, pooled, and barcoded DNA sequencing or any other sequencing method now known or yet to be disclosed; or any other method that allows the detection of a particular nucleic acid sequence within a sample or enables the differentiation of one nucleic acid from another nucleic acid that differs from the first nucleic acid by one or more nucleotides, or any combination of these.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP) are added to each of four reactions (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfurylase enzyme converts pyrophosphate into ATP which, in turn, catalyzes the conversion of luciferin to oxyluciferin which results in the generation of visible light that is then detected by a camera.

In SOLID sequencing, the molecule to be sequenced is fragmented and used to prepare a population of clonal magnetic beads (in which each bead is conjugated to a plurality of copies of a single fragment) with an adaptor sequence, and alternatively, a barcode sequence. The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

(d) Preferred Embodiments

A group of exemplary embodiments is shown in Table A. The present invention provides, in one embodiment, that assay 1—nuc-Sa assay, applying primer set 1 represented by SEQ ID NO. 1 and 2 and/or probe 1 represented by SEQ ID NO. 3, may be carried out to identify and differentiate *S. aureus*, CNS and other species.

In another embodiment, assay 2—femA-Sa assay, applying primer set 2 represented by SEQ ID NO. 4 and 5 and/or probe 2 represented by SEQ ID NO. 6, may be carried out to identify and differentiate *S. aureus*, CNS and other species.

In one embodiment, assay 3—femA-Se assay, applying primer set 3 represented by SEQ ID NO. 7 and 8 and/or probe 3 represented by SEQ ID NO. 9, may be carried out to identify and differentiate *S. epidermis* from other *Staphylocossus* species.

In one embodiment, assay 4—tuf-Sa assay, applying primer set 4 represented by SEQ ID NO. 10 and 11 and/or probe 4 represented by SEQ ID NO. 12, may be carried out to identify *S. aureus*.

In one embodiment, assay 5—tuf-CNS assay, applying primer set 5 represented by SEQ ID NO. 13 and 14 and/or probe 5 represented by SEQ ID NO. 15, may be carried out to identify CNS.

In one embodiment, assay 6—mecA assay, applying primer set 6 represented by SEQ ID NO. 16 and 17 and/or probe 6 represented by SEQ ID NO. 18, may be carried out to identify and differentiate methicillin and penicillin resistance phenotypes.

In one preferred embodiment, a multiplex assay—tuf differential multiplex assay, combining tuf-Sa assay (assay 4) and tuf-CNS assay (assay 5) illustrated above by applying both sets of primers and probes in one RT-PCR reaction, may be used to differentiate *S. aureus* and CNS.

Another preferred multiplex assay for identifying and differentiating MRSA, MSSA, MRSE or MSSE in a sample comprises femA-Se assay (assay 3); mecA assay (assay 6); and at least one assay chosen from the nuc-Sa assay (assay 1) and femA-Sa assay (assay 2).

Yet another preferred multiplex assay for identifying and differentiating MRSA, MSSA, MRSE, MSSE, MRCNS or MSCNS in a sample comprises mecA assay (assay 6) and two assays chosen from femA-Se assay (assay 3), tuf-Sa assay (assay 4), and tuf-CNS assay (assay 5).

The combination of assays in a multiplex RT-PCR/PCR assay is through applying multiple sets of primers and/or probes, respectively, in one RT-PCR reaction. The multiplex RT-PCR/PCR assay may comprise any number or any combination of individual assays, even if some of the assays are redundant in purposes but serve as a verification tool.

In some other embodiments, the individual assays (assays 1-6) disclosed herein may also be carried out separately, however the results of these individual assays may be superimposed and comparable after internal control normalization.

(III) Kits.

Still another aspect of the invention encompasses kits for identifying and differentiating MRSA, MSSA, MRCNS or MSCNS in a sample. In preferred embodiments, the kits comprise one or more primer sets and probes for assays chosen from nuc-Sa assay, femA-Sa assay, femA-Se assay, tuf-Sa assay, tuf-CNS assay and mecA assay. As described in detail in previous sections and in Table A: nuc-Sa assay for identifying and differentiating *S. aureus* and other species by applying primer set 1, represented by SEQ ID NO. 1 and 2, and/or probe 1, represented by SEQ ID NO. 3; femA-Sa assay for identifying and differentiating *S. aureus* and other species by applying primer set 2, represented by SEQ ID NO. 4 and 5, and/or probe 2, represented by SEQ ID NO. 6; femA-Se assay for identifying and differentiating *S. epidermis* from other *Staphylocossus* species by applying primer set 3, represented by SEQ ID NO. 7 and 8, and/or probe 3, represented by SEQ ID NO. 9; tuf-Sa assay for identifying *S. aureus* by applying primer set 4, represented by SEQ ID NO. 10 and 11, and/or probe 4, represented by SEQ ID NO. 12; tuf-CNS assay for identifying CNS by applying primer set 5, represented by SEQ ID NO. 13 and 14, and/or probe 5, represented by SEQ ID NO. 15; and mecA assay for identifying and differentiating methicillin and penicillin resistance phenotypes by applying primer set 6, represented by SEQ ID NO. 16 and 17, and/or probe 6, represented by SEQ ID NO. 18.

The multiplex assay is a type of analysis chosen from PCR, RT-PCR, sequencing, hybridization, and any combination thereof, in which a primer set or a probe or both is applied to detect the presence or absence of and at least one other targeted sequences chosen from nuc-*S. aureus* gene, femA-*S. aureus* gene, femA-*S. epidermis*, tuf-*S. aureus* gene, tuf-CNS gene, and mecA gene. The assays detecting respective targeted genes may be carried out individually in multiple separate reaction systems, or in one combined and mixed reaction system for PCR, RT-PCR, sequencing, hybridization, or any combination thereof.

In one preferred embodiment, the kit comprises primer sets and probes for a multiplex assay, such as tuf differential multiplex assay, which combines tuf-Sa assay and tuf-CNS assay by applying both sets of primers and/or probes in one RT-PCR reaction to differentiate *S. aureus* and CNS.

In one preferred embodiment, the kit for identifying and differentiating MRSA, MSSA, MRCNS or MSCNS in a sample by multiplex assay comprises primer sets and probes for femA-Se assay, mecA assay and for at least one other assay chosen from the nuc-Sa assay and femA-Sa assay.

Yet in another preferred embodiment, the kit for identifying and differentiating MRSA, MSSA, MRCNS or MSCNS in a sample by a multiplex assay comprises primer sets and probes for mecA assay and two other assays chosen femA-Se assay, tuf-Sa assay, and tuf-CNS assay.

The kits that facilitate nucleic acid based assays may further comprise one or more of the following: nucleic acid extraction reagents, controls, disposable cartridges, labeling reagents, enzymes including PCR amplification reagents such as the DNA polymerases Taq or Pfu, reverse transcriptase, or one or more other polymerases, and/or reagents that facilitate hybridization.

In another embodiment, the kit may further comprise a label that can be used to label the primer or probe oligonucleotide. A label may be any substance capable of aiding a machine, detector, sensor, device, or enhanced or unenhanced human eye, in differentiating a sample that displays positive expression from a sample that displays reduced expression. Examples of labels include, but are not limited to: a radioactive isotope or chelate thereof, a dye (fluorescent or nonfluorescent,) stain, enzyme, or nonradioactive metal. Specific examples include, but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylaminophenylazo) benzoic acid ("Dabcyl"); 4-(4'-dimethyl-amino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylene diamine tetra-acetic acid ("EDTA") and derivatives thereof, or any other compound that signals the presence of the labeled nucleic acid. In one embodiment of the invention, the label includes one or more dyes optimized for use in genotyping. Examples of such dyes include, but are not limited to: dR110, 5-FAM, 6FAM, dR6G, JOE, HEX, VIC, TET, dTAMRA, TAMRA, NED, dROX, PET, BHQ+, Gold540, and LIZ.

In yet another embodiment, the primers and probes in the kit may have been labeled, and can be applied without a labeling process in PCR, sequencing reaction, or binding to a solid substrate such as oligonucleotide array.

A kit for identifying and differentiating MRSA, MSSA, MRSE, MSSE, MRCNS and MSCNS in a sample may also comprise instructions for use. In one embodiment, the kit may further comprise an indication that links the output of the assays provided by the kit to a particular result. For example, an indication may provide guide to associate the presence or absence of one or more sequences to the identification of a particular bacterial phylum, class, order, family, genus species, subspecies, strain, or any other delineation of a group of bacteria. The indication may contain a standard curve configured to quantify the amount of bacterium present in a sample. The output of the assay may be in a form of a particular sequence, a particular genotype, a particular ΔCt level in a real-time quantitative PCR reaction, a level of fluorescence or radioactive decay, a value derived from a standard curve, or from a positive or negative control, or any combination of these and other outputs. The indication may be printed on a writing that may be included in the kit, or it may be posted on the Internet, or embedded in a software package. The writing may include graphical depictions of results such as a photomicrograph or amplification plot.

A kit for identifying and differentiating MRSA, MSSA, MRSE, MSSE, MRCNS and MSCNS in a sample may further comprise a device used to collect the sample. Such devices may include but need not be limited to: swabs, needles, blood collection tubes, wipes, or any other apparatus that may be used to collect a biological sample from a patient or from the environment now known or yet to be disclosed.

EXAMPLES

The following examples illustrate certain aspects of the invention.

Example 1—Specificity and Selectivity

The present invention discloses real time PCR assays designed to differentiate between MRSA, MSSA, MRSE, MSSE, MRCNS and MSCNS in mixed specimens using specific combinations of up to 4 assays depending on the application. The performance of the individual assays using panels of bacterial isolates is shown in Tables 2-6. All of the assays have been shown to be highly sensitive and specific. Assays to identify MSSA and MRSA are included in the screening assay. While MSSA infections are generally easier to treat, they remain a significant factor in hospital acquired infections. In addition colonization with either MRSA or MSSA has been shown to increase the risk of infection. MSSA, MRSA and CoNS assays are included in the diagnostic assay as all are major factors in surgical infection, bacteremia and implantable device infection, with both MRCNS and MSCNS becoming an increasing problem.

These assays may be used in combination to identify MRSA using the nuc and femA-*S. aureus* genes as markers to detect *S. aureus*, using the tuf gene as a marker to differentiate *S. aureus* from Coagulase Negative *Staphylococcus* (CNS), using the femA-*S. epi* gene as a marker to rule out *Staphylococcus epidermis*, and using the mecA gene as a marker to determine methicillin/penicillin resistance. For Coagulase Negative *Staphylococcus*, primers represented by SEQ ID NO. 13, SEQ ID NO. 14, and SEQ ID NO. 15, from the tuf gene of the CNS species *Staphylococcus capitis, S. epidermidis, S. haemolyticus, S. hominis, S. lugdunensis, S. saprophyticus, S. simulans,* and *S. warneri* were aligned in order to design the primers used in the assay to detect CNS (Table 1 and Table 5). The assay using SEQ ID NO. 13, SEQ ID NO. 14, and SEQ ID NO. 15 may detect the tuf gene in any of the listed CNS species.

TABLE 1

Primer and probe sets

| Target | Description | Sequence | SEQ ID NO. |
|---|---|---|---|
| nuc | nuc_forward | CCAAGCCTTGACGAACTAAAGCT | 1 |
|  | nuc_reverse | GGTCCTGAAGCAAGTGCATTTAC | 2 |
|  | nuc_Probe | CAGCATAAATATACGCTAAGCCACGTCCA | 3 |
| femA-*S. aureus* | femA_*S.aureus*_F | TCAAATCGCGGTCCAGTGAT | 4 |
|  | femA_*S.aureus*_R | ATTACCTGTAATCTCGCCATCATGA | 5 |
|  | femA_Sa_probe | CATCGTTGTCTATACCTACATATC | 6 |
| femA-*S. epi* | femA_*S.epi*_F | GCTGGTGGAACTTCAAATCGTTA | 7 |
|  | femA_*S.epi*_R | CGATTAATACCATGTTCAATTGCATAG | 8 |
|  | femA_*S.epi*_probe | TTTGCAGGGAGCTATGCGGTTCAA | 9 |
| tuf* | tuf-*S.aureus*_F | AGAATTAATGGAAGCTGTAGATACTTACATTC | 10 |
|  | tuf-*S.aureus*_R | CTGTAACAGTTGTTTTAGATGTGTCATGTAA | 11 |
|  | tuf-*S.aureus*_Probe | CTCCAGAACGTGATTCTGACAAACCATTCA | 12 |
|  | tuf-CNS_F | GCTCAAAAGAACATGCCAATATTG | 13 |
|  | tuf-CNS_R | TAATACAGTTGCGATAGCAGCTGTT | 14 |
|  | tuf-CNS_Probe | AAAGTWGTTTTACCATGGTCAACGTGACCG | 15 |
| mecA | mecA_F | GGAACGATGCCTATCTCATATGCT | 16 |
|  | mecA_R | ATAGCGTCATTATTCCAGGAATGCA | 17 |
|  | mecA_Probe | TTGGCCAATTCCACATTGTTTCGGTC | 18 |

TABLE 2

Detection of *S. aureus*, CNS, and other species using femA-
*S. aureus* assay (SEQ ID NO. 4, SEQ ID NO. 5, SEQ ID NO. 6).

| Results: | *S. aureus* | CNS | Other |
|---|---|---|---|
| Detected | 55 | 3 | 0 |
| Did not detect | 4 | 94 | 83 |
| Total screened | 59 | 97 | 83 |

TABLE 3

Detection of *S. aureus*, CNS, and other species using
nuc assay (SEQ ID NO. 1, SEQ ID NO. 2, and SEQ ID NO. 3)

| Results: | *S. aureus* | CNS | Other |
|---|---|---|---|
| Detected | 56 | 3 | 0 |
| Did not detect | 3 | 94 | 83 |
| Total screened | 59 | 97 | 83 |

TABLE 4

Detection of *S. epidermis* using femA- *S. epidermis*
assay (SEQ ID NO. 4, SEQ ID NO. 5, and SEQ ID NO. 6).

| Results: | *S. epidermidis* | Other *Staph* | Other |
|---|---|---|---|
| Detected | 34 | 25 | 2 |
| Did not detect | 4 | 93 | 81 |
| Total screened | 38 | 118 | 83 |

TABLE 5

Detection of *S. aureus* (SEQ ID NO. 10, SEQ ID NO. 11, and
SEQ ID NO. 12), or CNS using tuf differential multiplex assay
(SEQ ID NO. 13, SEQ ID NO. 14, and SEQ ID NO. 15).

| Results: | *S. aureus* | CNS | Other |
|---|---|---|---|
| *S. aureus* assay detected | 55 | 3 | 0 |
| *S. aureus* assay did not detect | 4 | 94 | 83 |
| CNS assay detected | 2 | 92 | 4 |
| CNS assay did not detect | 57 | 5 | 79 |

TABLE 6

Detection of methycillin resistant *Staphylococcus aureus*
using the mecA assay (SEQ ID NO. 16, SEQ ID
NO. 17, and SEQ ID NO. 18).

| Results: | Resistant | Susceptible | Unknown |
|---|---|---|---|
| Detected | 60 | 1 | 3 |
| Did not detect | 0 | 25 | 0 |
| Total screened | 60 | 26 | 3 |

The disclosed assays, as shown in the above tables include: (1) femA-*S. aureus* assay to detect *S. aureus*, CNS, and other species using primers represented by SEQ ID NO. 4, SEQ ID NO. 5, SEQ ID NO. 6 (Table 2); (2) nuc assay to detect *S. aureus*, CNS, and other species using primers represented by SEQ ID NO. 1, SEQ ID NO. 2, and SEQ ID NO. 3 (Table 3); (3) femA-*S. epidermis* assay to detect *S. epidermis* using primers represented by SEQ ID NO. 4, SEQ ID NO. 5, and SEQ ID NO. 6 (Table 4); (4) tuf differential multiplex assay to detect *S. aureus* using SEQ ID NO. 10, SEQ ID NO. 11, and SEQ ID NO. 12, or to detect CNS using primers represented by SEQ ID NO. 13, SEQ ID NO. 14, and SEQ ID NO. 15 (Table 5); and (5) mecA assay to detect methicillin resistant *Staphylococcus aureus* (MRSA) using the primers represented by SEQ ID NO. 16, SEQ ID NO. 17, and SEQ ID NO. 18 (Table 6).

In addition, a broader CoNS assay was being used and the performance of the CoNS assay is reflected in the following Table 7 A-D.

TABLE 7 A

*S. Aureus* Assay 1 for *S. aureus* identification

| Results: | *S. aureus* | CNS | Other | |
|---|---|---|---|---|
| Detected | 57 | 0 | 0 | |
| Did not detect | 1 | 97 | 83 | |
| Total screened | 58 | 97 | 83 | 238 |

TABLE 7 B

*S. Aureus* Assay 2 for *S. aureus* identification

| Results: | *S. aureus* | CNS | Other | |
|---|---|---|---|---|
| Detected | 58 | 0 | 0 | |
| Did not detect | 0 | 97 | 83 | |
| Total screened | 58 | 97 | 83 | 238 |

TABLE 7 C mecA Assay for mecA gene detection

| Results: | Resistant | Susceptible | Unknown | |
|---|---|---|---|---|
| Detected mecA | 86 | 0 | 0 | |
| Did not detect mecA | 4* | 53 | 0 | |
| Total *S. aureus* screened | 90 | 53 | 0 | 143 |

TABLE 7 D

Detecting *S. aureus* or CNS using differential multiplex

| Results: | *S. aureus* | CNS | Other | |
|---|---|---|---|---|
| *S. aureus* assay detected | 58 | 0 | 0 | |
| *S. aureus* assay did not detect | 0 | 97 | 83 | |
| CNS assay detected | 0 | 96 | 2 | |
| CNS assay did not detect | 58 | 1 | 81 | |
| Total screened | 58 | 97 | 83 | 238 |

The above assays shown in Table 2-7 may be used individually, in any combination with each other, or with additional assays, to ascertain whether or not MRSA is present in a sample. This includes performance of all assays separately, in a single PCR run, in a single sequencing reaction, on a single array, or in any other combination now known or yet to be disclosed. Species tested in these assays include, but are not limited to: *S. aureus*, *S. epidermidis*, *S. haemolyticus*, *S. saprophyticus*, *S. capitis*, *S. lugdunensis*, *S. xylosus*, *S. equorum*, *S. hominis*, *S. kloosi*, *S. gallinarium*, *S. chonii*, and *S. arlettae*.

Example 2—Differential Ct Values Differentiating MRSA, MSSA, MRSE, and MSSE Including Mixtures Thereof Employing multiple assays with similar efficiencies, the mecA gene can be tied to either SA or CoNS through the use of relative Ct values. The amplification plots illustrated in FIGS. 1-6, show how the assay amplifications are tied together to produce a result. The specimens used to generate these example plots were a cohort of 50 remnant respiratory specimens; throat swabs, nasal swabs or sputum. The results show a strong correlation between culture results and PCR results, see Table 8.

The methodology for identifying and differentiating MSSA, MRSA and CoNS employed in the assays disclosed herein avoids some of the pitfalls which have been documented when using the SCCmec cassette insertion as a target, such as, empty cassette false positives (Wang H. JCM 2010; 48:3528) and missed clonal type false negatives. (Peterson LR. JCM 2010; 48:1661). In addition, the assays disclosed herein provide clinical information, both for screening and diagnostics, that is highly relevant to clinical questions and is not available from other commercially available MRSA assays.

FIGS. 1-6 display a set of combined amplification plots that illustrate how the disclosed assays work in combination to directly identify MRSA, MSSE, MRSE, and MSSE in clinical samples. The results are separate assays superimposed onto a single amplification plot. Given the type of specimen, respiratory, many were mixed specimens which served to challenge and illustrate the assays ability to identify and differentiate *S. aureus* and *S. epidermidis* with and without the mecA gene. While two different *S. aureus* assays are shown, i.e., femA and nuc assays, they are redundant and useful for the purpose of comparatively evaluating assay performance. One *S. aureus* assay, either femA or nuc, and the mecA assay may be used to identify and differentiate MSSA and MRSA. The particular plots in FIG. 1-6 use a *S. epidermidis* assay. A broader CoNS assay was used and the performance of that assay is reflected in Example 1 Table 7 A-D.

FIG. 1 depicts the results of a set of real-time PCR assays used to analyze the throat swab sample designated TG6604. The assay used to detect the presence of nuc (SEQ ID NO. 1, SEQ ID NO. 2, and SEQ ID NO. 3) resulted in a Ct of 33.2. The assay used to detect the presence of *S. aureus* femA (SEQ ID NO. 4, SEQ ID NO. 5, and SEQ ID NO. 6) resulted in a Ct of 33.6. Both of these results indicate that the sample included *S. aureus*. The assay used to detect the presence of mecA (SEQ ID NO. 16, SEQ ID NO. 17, and SEQ ID NO. 18) showed no amplification. The assay to detect the presence of *S. epidermidis* femA (SEQ ID NO. 7, SEQ ID NO. 8, and SEQ ID NO. 9) also showed no amplification. In summary, this sample contained *S. aureus*, but the *S. aureus* present was not methicillin resistant. The sample did not contain *S. epidermidis*. Therefore, samples showing this pattern of amplification may be classified as methicillin-sensitive *S. aureus* (MSSA).

Figure 2:
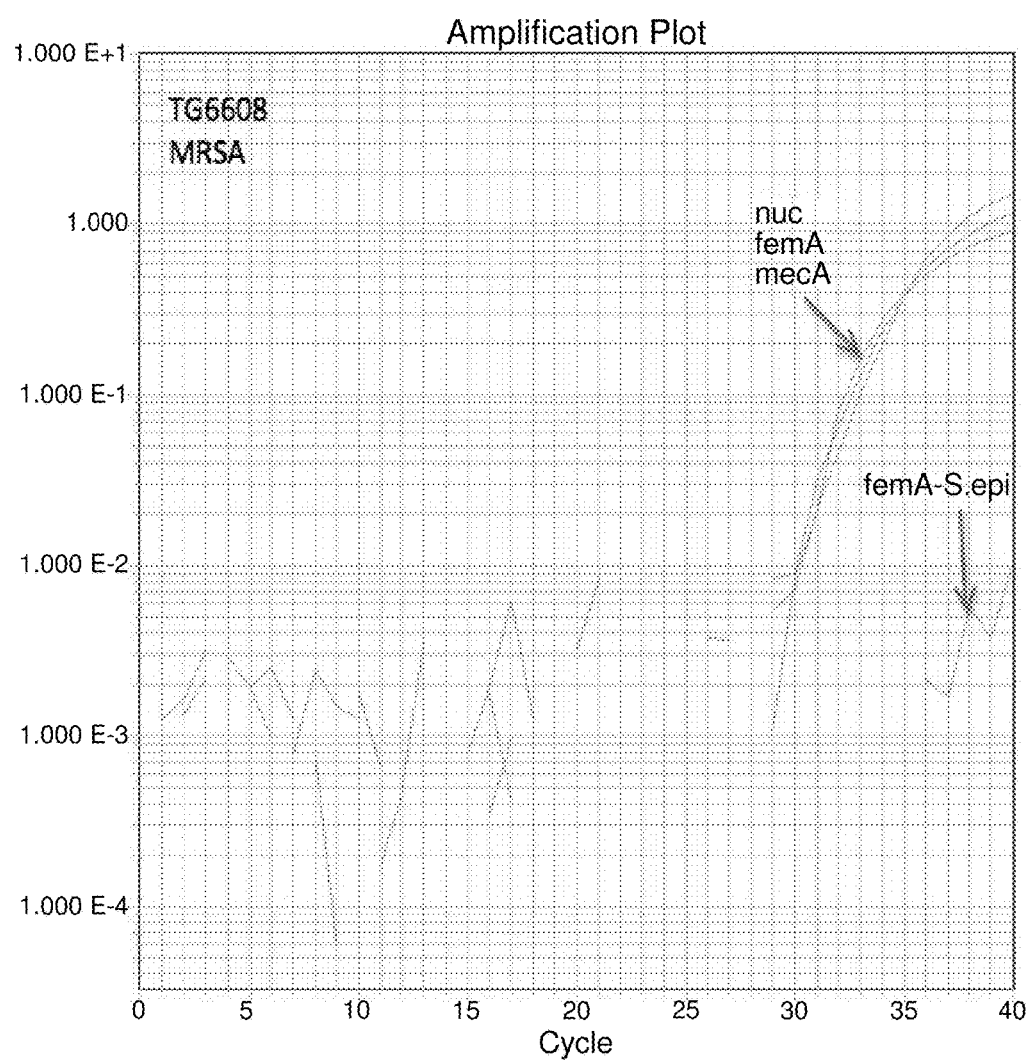
FIG. 2 depicts the results of four real-time PCR assays comprising nuc-Sa, femA-SA, femA-Sepi and mecA assays; the multiplex assay was used to analyze the throat swab sample designated TG6608.

FIG. 2 depicts the results of a set of real-time PCR assays used to analyze the throat swab sample designated TG6608. The assay to detect the presence of nuc resulted in a Ct of 33.6. The assay to detect the presence of *S. aureus* femA resulted in a Ct of 33.5. The assay to detect the presence of mecA resulted in a Ct of 33.9. The assay to detect the presence of *S. epidermidis* femA showed no amplification. In summary, this sample contained *S. aureus* that is methicillin resistant. The sample did not contain *S. epidermidis*. Samples showing this pattern of amplification may be classified as methicillin-resistant *S. aureus* (MRSA.) The presence of MRSA was confirmed through bacterial culture.

Figure 3:
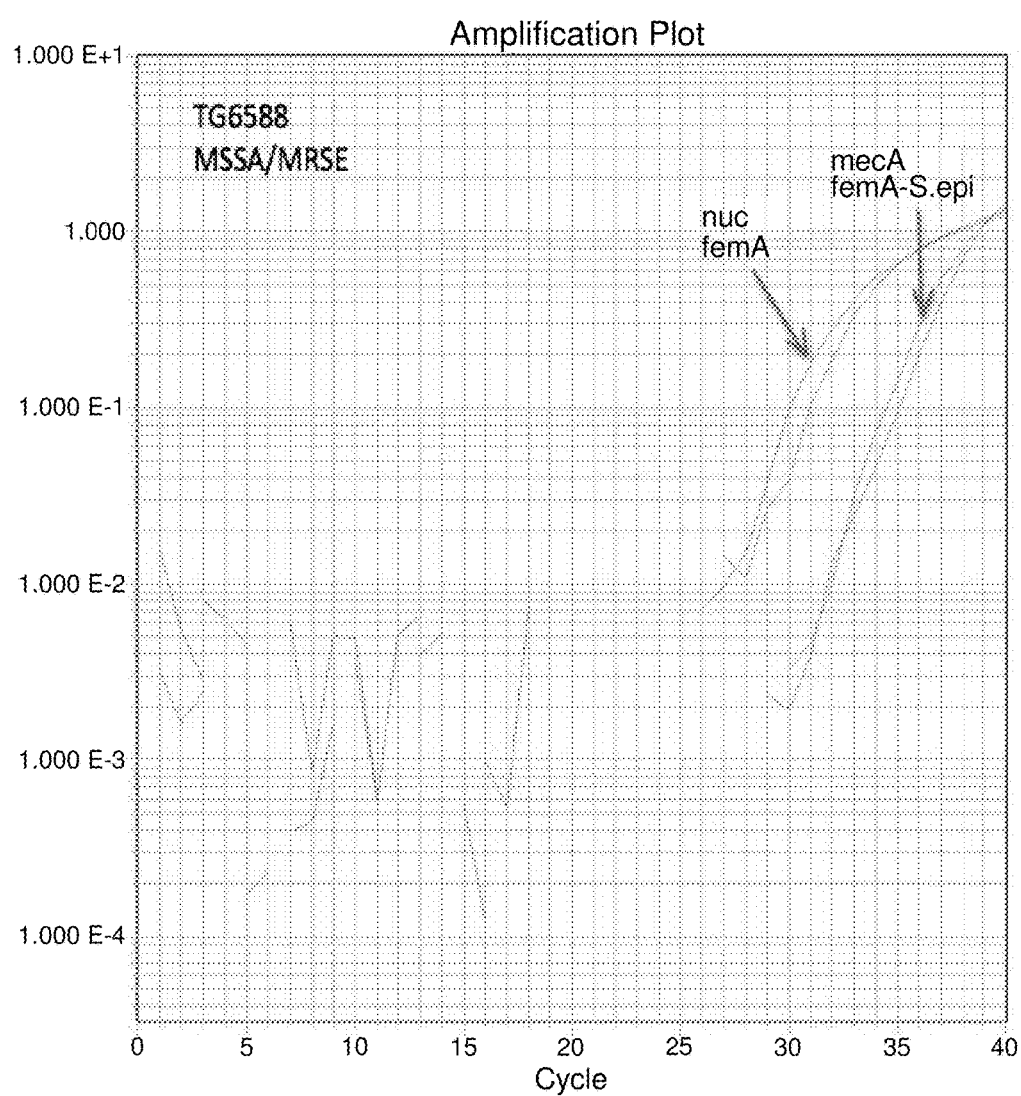
FIG. 3 depicts the results of four real-time PCR assays comprising nuc-SA, femA-SA, femA-Sepi and mecA assays; the multiplex assay was used to analyze the throat swab sample designated TG6588.

FIG. 3 depicts the results of a set of real-time PCR assays used to analyze the throat swab sample designated TG6588. The assay to detect the presence of nuc resulted in a Ct of 32.0. The assay to detect the presence of *S. aureus* femA resulted in a Ct of 31.3. The assay to detect the presence of mecA resulted in a Ct of 35.2. The assay to detect the presence of *S. epidermidis* femA resulted in a Ct of 35.9. In summary, this sample contained both *S. aureus* and *S. epidermidis*. Because the amplification of the mecA has a similar Ct as that of the *S. epidermis* femA, the methicillin resistance is a characteristic of the *S. epidermidis* and not the *S. aureus*. Samples showing this pattern of amplification may be classified as containing a mixture of methicillin sensitive *S. aureus* (MSSA) and methicillin resistant *S. epidermidis* (MRSE).

Figure 4:
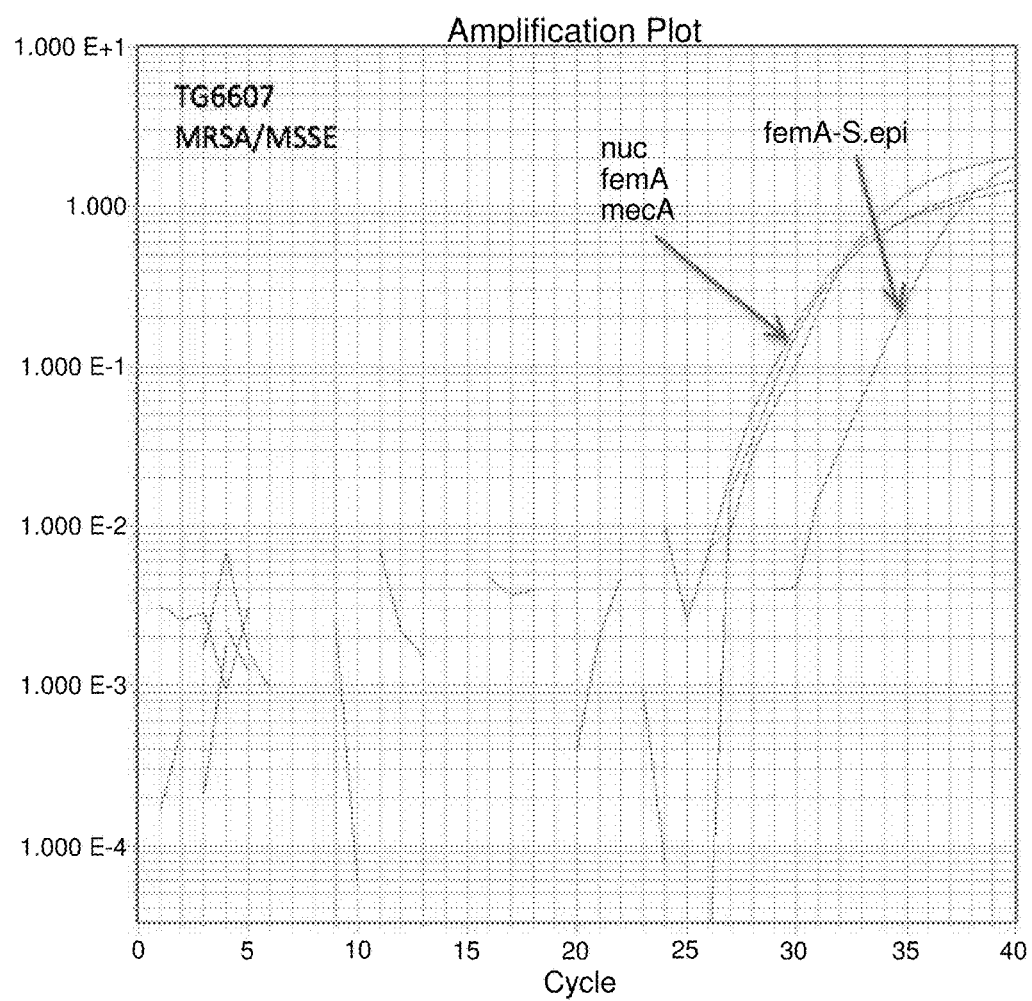
FIG. 4 depicts the results of four real-time PCR assays comprising nuc-SA, femA-SA, femA-Sepi and mecA assays; the multiplex assay was used to analyze the throat swab sample designated TG6607.

FIG. 4 depicts the results of a set of real-time PCR assays used to analyze the throat swab sample designated TG6607. The assay to detect the presence of nuc gene resulted in a Ct of 30.1. The assay to detect the presence of *S. aureus* femA resulted in a Ct of 30.3. The assay to detect the presence of the mecA gene resulted in a ΔCt of 30.8. The assay to detect the presence of the *S. epidermidis* femA gene resulted in a ΔCt of 34.6. In summary, this sample contains both *S. aureus* and *S. epidermidis*. Because the amplification of the mecA has a similar Ct to that of the *S. aureus* femA, the methicillin resistance is a characteristic of *S. aureus* and not *S. epidermidis*. Samples showing this pattern of amplification may be classified as containing a mixture of methicillin resistant *S. aureus* (MRSA) and methicillin-sensitive *S. epidermidis* (MSSE).

Figure 5:
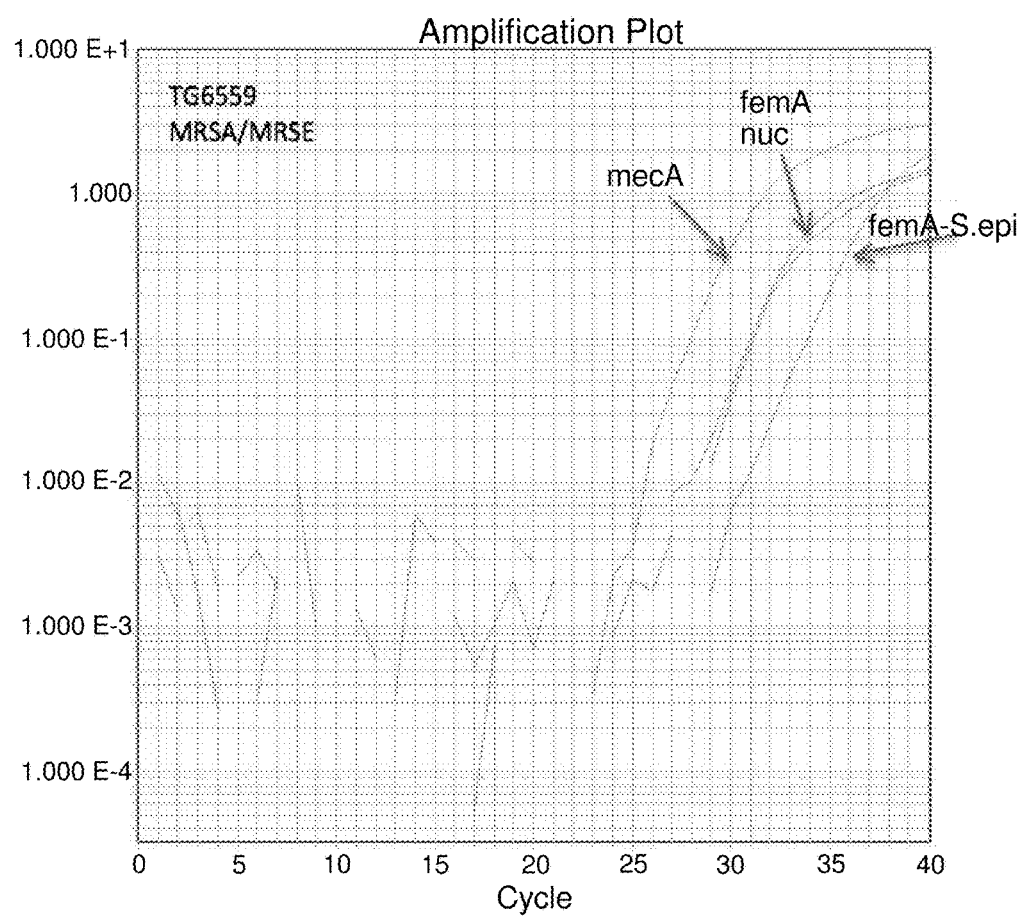
FIG. 5 depicts the results of four real-time PCR assays comprising nuc-SA, femA-SA, femA-Sepi and mecA assays; the multiplex assay was used to analyze the throat swab sample designated TG6759.

FIG. 5 depicts the results of a set of real-time PCR assays used to analyze the throat swab sample designated TG6759. The assay to detect the presence of the nuc gene resulted in a Ct of 31.9. The assay to detect the presence of the *S. aureus* femA gene resulted in a Ct of 32.1. The assay to detect the presence of the mecA gene resulted in a Ct of 28.8. The assay to detect the presence of the *S. epidermidis* femA gene resulted in a Ct of 34.8. In summary, this sample contained both *S. aureus* and *S. epidermidis*. Because the amplification of mecA occurred earlier than the nuc, *S. aureus* femA and *S. epidermidis* femA assays, methicillin resistance is a characteristic of both the *S. aureus* and *S. epidermidis* contained in the sample. This is due to the additive effect of the mecA gene occurring in both the *S. aureus* and *S. epidermidis*. Samples showing this pattern of amplification may be classified as containing a mixture of methicillin resistant *S. aureus* (MRSA) and methicillin-resistant *S. epidermidis* (MRSE).

Figure 6:
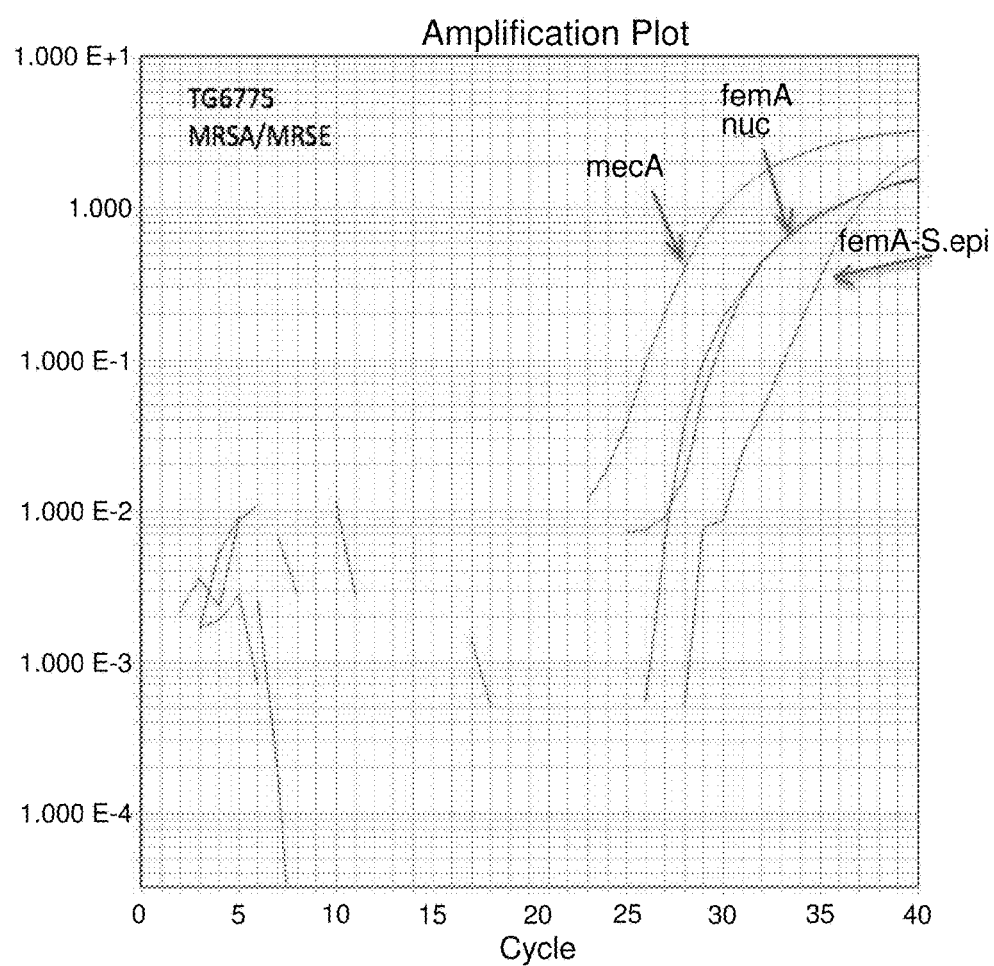
FIG. 6 depicts the results of four real-time PCR assays comprising Nuc-SA, femA-SA, femA-Sepi and mecA assays; the multiplex assay was used to analyze the throat swab sample designated TG6775.
Figure 7:
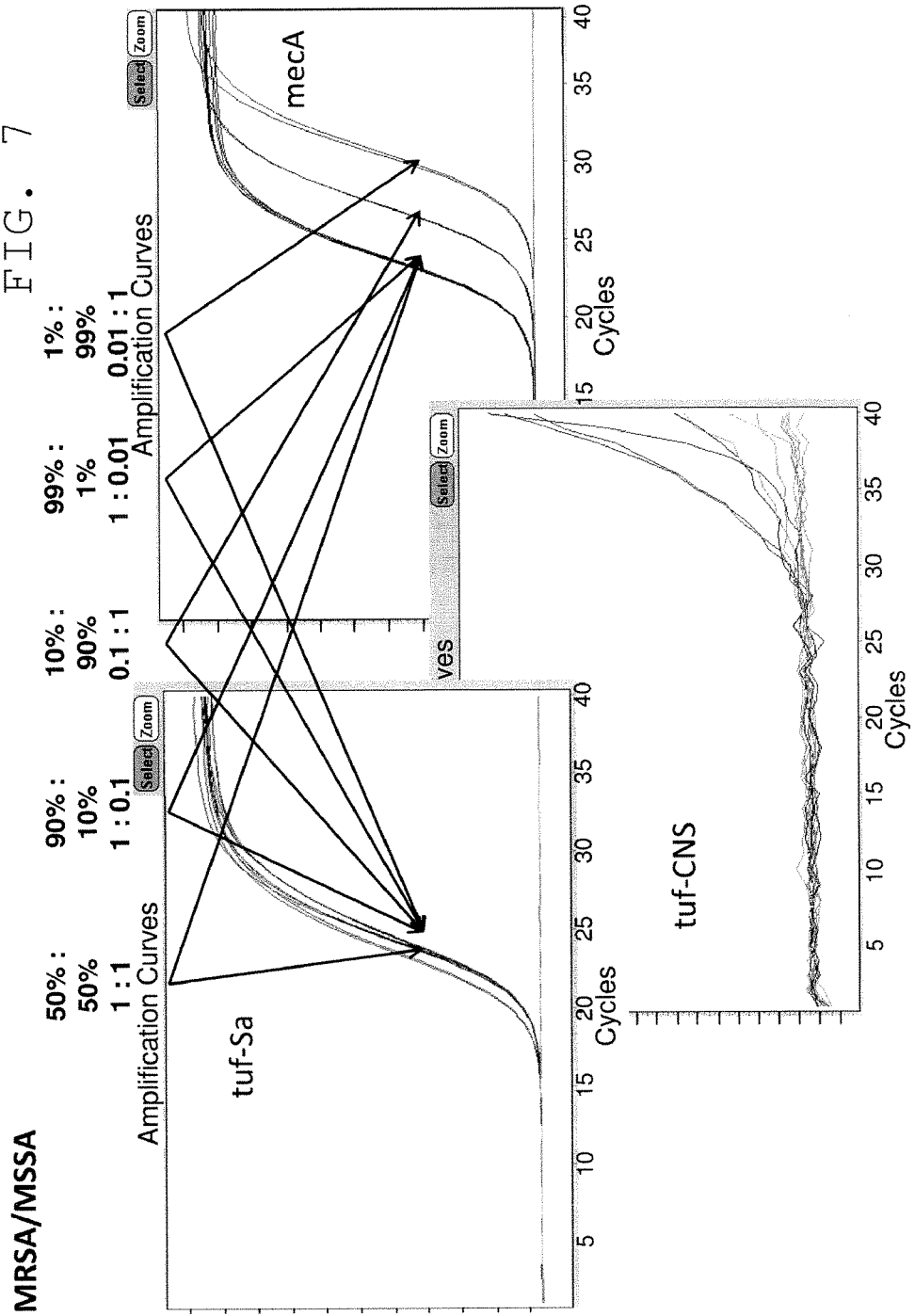
FIG. 7 depicts the results and the amplification curve pattern of a real-time PCR multiplex assay comprising femA-Sa, nuc-Sa, tuf-Sa, tuf-CNS, and mecA assays; the multiplex assay was used to analyze the MRSA/MSSA group samples including mixtures of MRSA and MSSA in 1:1, 1:0.1, 0.1:1, 1:0.01, and 0.01:1 ratio. The gradation of the y axis of each graph from bottom to top is 0.094, 0.394, 0.694, 0.994, 1.294, 1.594, 1.894, 2.194, 2.494, 2.794, and 3.094, respectively for the tuf-Sa graph; 3.226, 4.226, 5.226, 6.226, 7.226, 8.226, 9.226, and 10.226, respectively for the mecA graph; and −0.086, 0.014, 0.114, 0.214, 0.314, 0.414, 0.514, 0.614, 0.714, 0.814, 0.914, and 1.014, respectively for the tuf-CNS graph.
Figure 8:
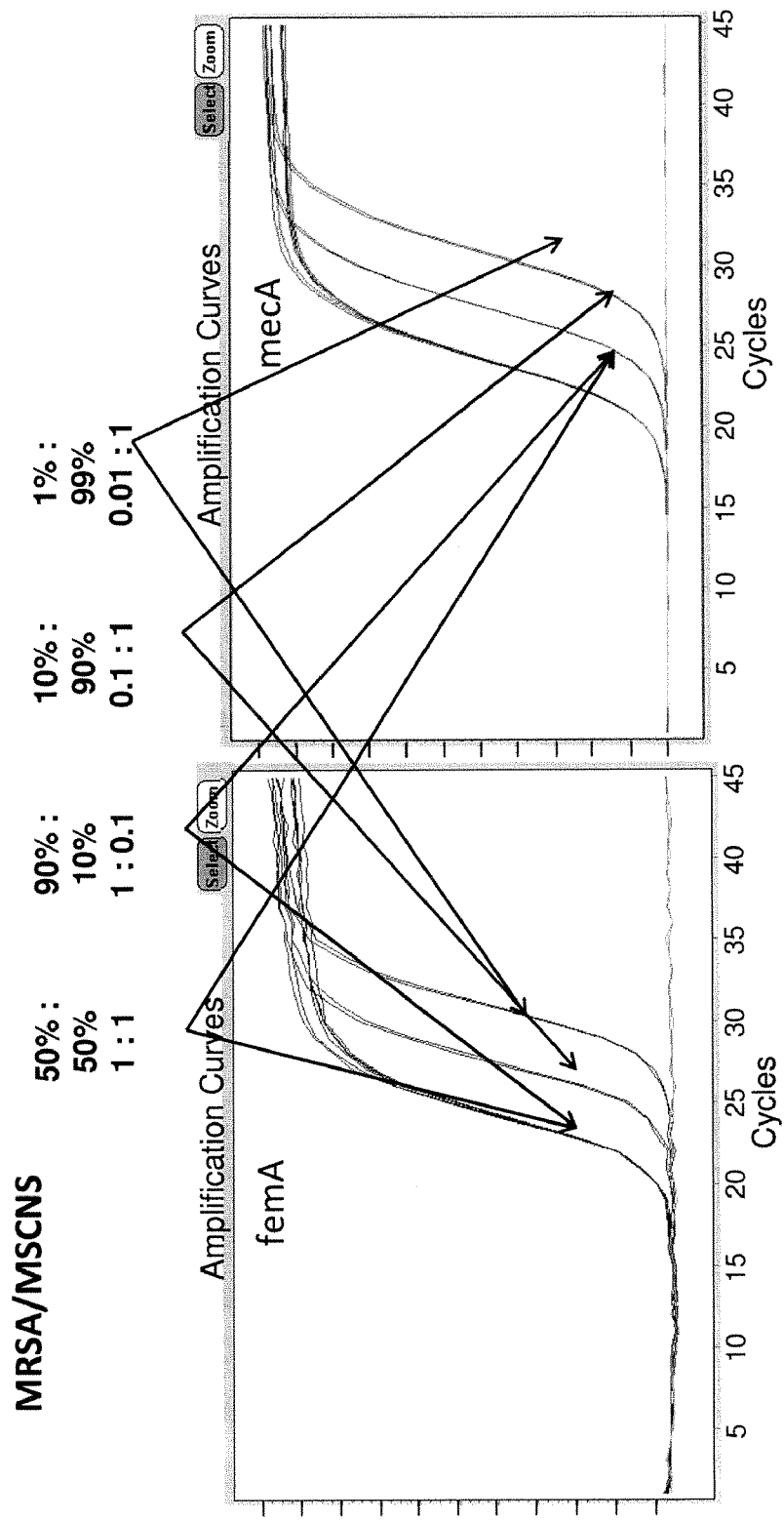
FIG. 8 depicts the results and the amplification curve pattern of a real-time PCR multiplex assay comprising femA-Sa, nuc-Sa, tuf-Sa, tuf-CNS, and mecA assays; the multiplex assay was used to analyze the MRSA/MSCNS group samples including mixtures of MRSA and MSCNS in 1:1, 1:0.1, 0.1:1, 1:0.01, and 0.01:1 ratio. The gradation of the y axis of each graph from bottom to top is 0.205, 0.805, 1.405, 2.005, 2.605, 3.205, 3.805, 4.405, 5.005, 5.605, and 6.205, respectively for the femA graph; and 0.019, 0.919, 1.619, 2.719, 3.619, 4.519, 5.419, 6.319, 7.219, 8.119, 9.019, and 9.919, respectively for the mecA graph.
Figure 9:
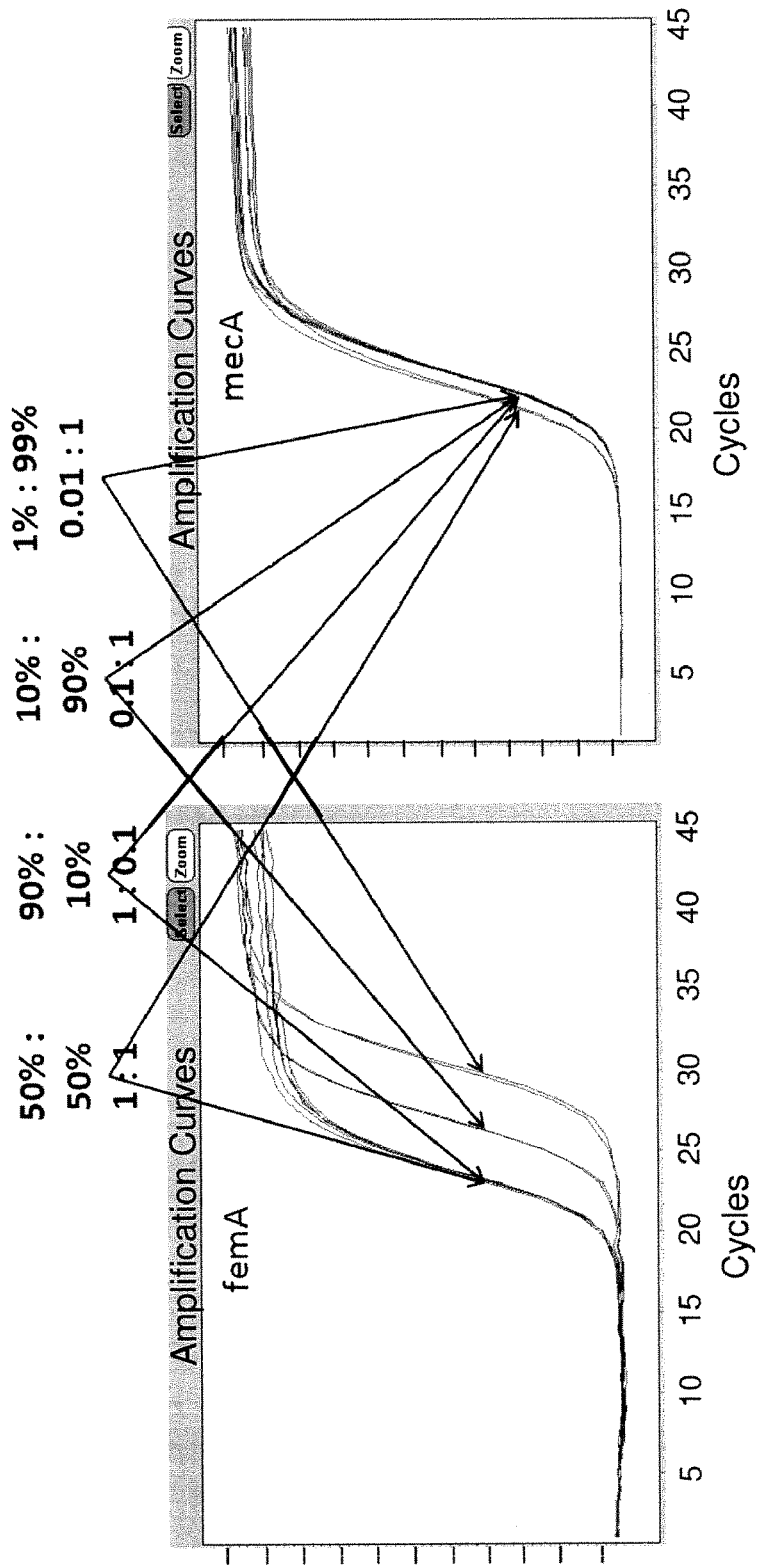
FIG. 9 depicts the results and the amplification curve pattern of a real-time PCR multiplex assay comprising femA-Sa, nuc-Sa, tuf-Sa, tuf-CNS, and mecA assays; the multiplex assay was used to analyze the MRSA/MRCNS group samples including mixtures of MRSA and MRCNS in 1:1, 1:0.1, 0.1:1, 1:0.01, and 0.01:1 ratio. The gradation of the y axis of each graph from bottom to top is 0.362, 0.962, 1.562, 2.162, 2.762, 3.362, 3.962, 4.562, 5.162, 5.762, and 6.362, respectively for the femA graph; and 0.210, 1.110, 2.010, 2.910, 3.810, 4.710, 5.610, 6.510, 7.410, 8.310, 9.210, and 10.110, respectively for the mecA graph.
Figure 10:
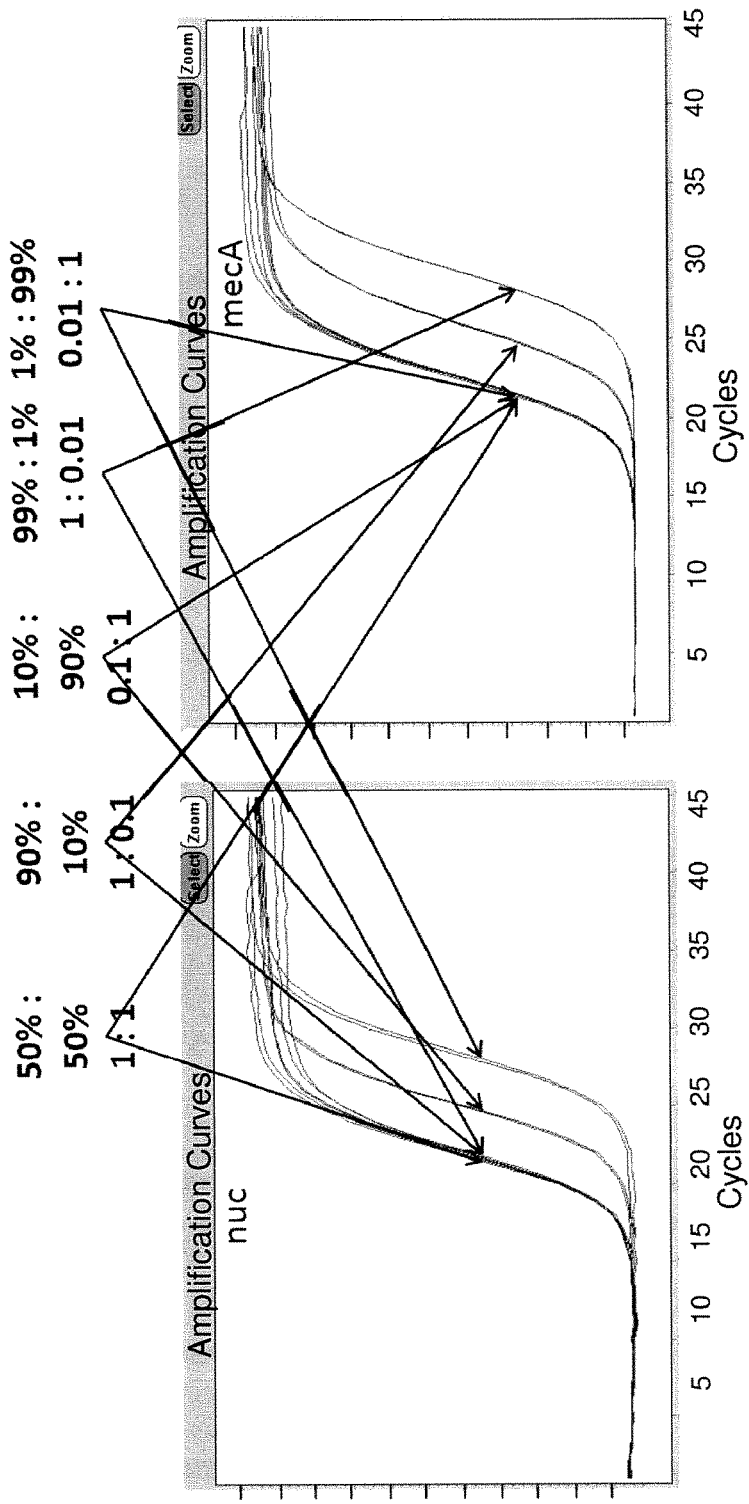
FIG. 10 depicts the results and the amplification curve pattern of a real-time PCR multiplex assay comprising femA-Sa, nuc-Sa, tuf-Sa, tuf-CNS, and mecA assays; the multiplex assay was used to analyze the MSSA/MRCNS group samples including mixtures of MSSA and MRCNS in 1:1, 1:0.1, 0.1:1, 1:0.01, and 0.01:1 ratio. The gradation of the y axis of each graph from bottom to top is 0.444, 1.444, 2.444, 3.444, 4.444, 5.444, 6.444, 7.444, 8.444, 9.444, and 10.444, respectively for the nuc graph; and 0.154, 1.154, 2.154, 3.154, 4.154, 5.154, 6.154, 7.154, 8.154, 9.154, and 10.154, respectively for the mecA graph.
Figure 11:
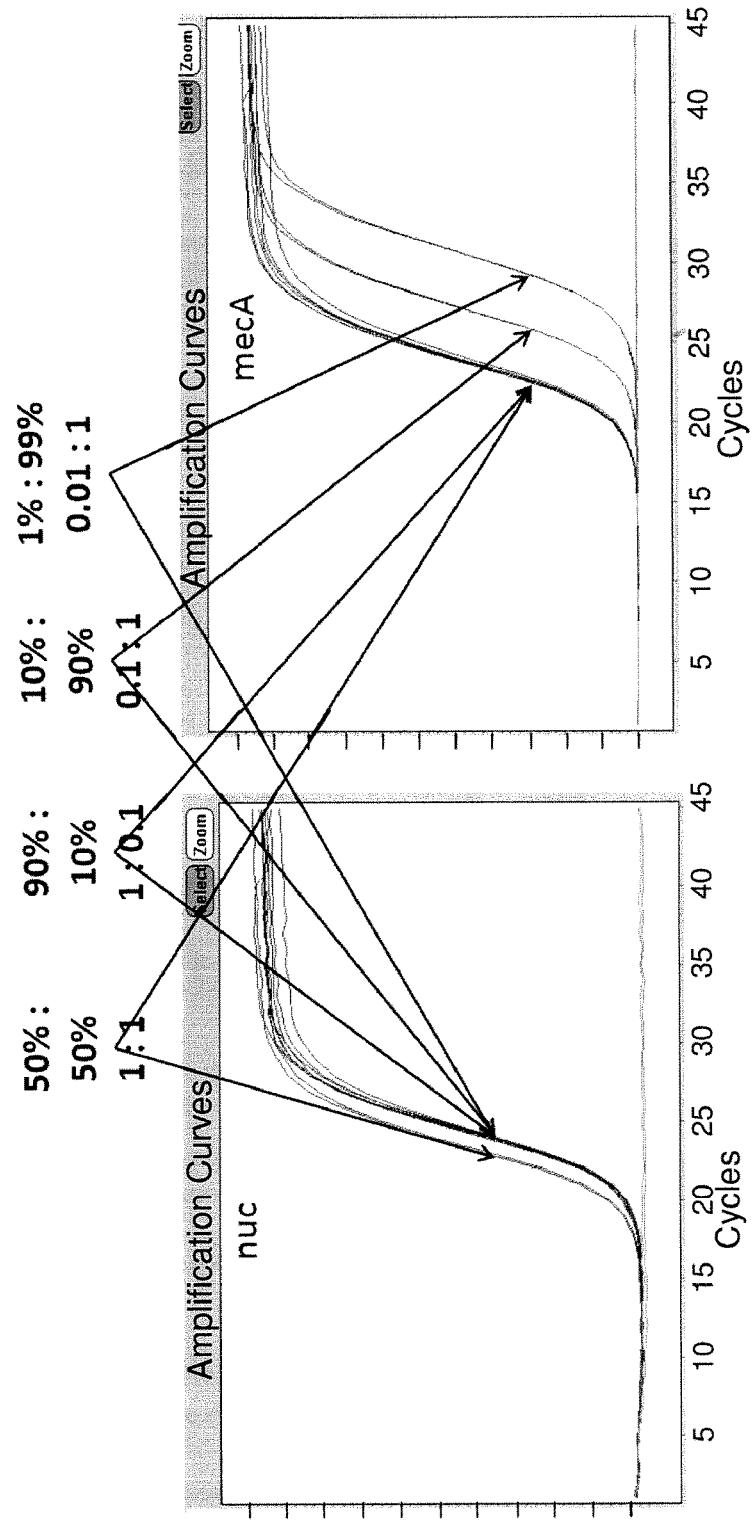
FIG. 11 depicts the results and the amplification curve pattern of a real-time PCR multiplex assay comprising femA-Sa, nuc-Sa, tuf-Sa, tuf-CNS, and mecA assays; the multiplex assay was used to analyze the MRSA/MSSA group samples including mixtures of MRSA and MSSA in 1:1, 1:0.1, 0.1:1, 1:0.01, and 0.01:1 ratio. The gradation of the y axis of each graph from bottom to top is 0.214, 1.214, 2.214, 3.214, 4.214, 5.214, 6.214, 7.214, 8.214, 9.214, and 10.214, respectively for the nuc graph; and −0.011, 0.889, 1.789, 2.689, 3.589, 4.489, 5.389, 6.289, 7.189, 8.089, 8.889, and 9.889, respectively for the mecA graph.
Figure 12:
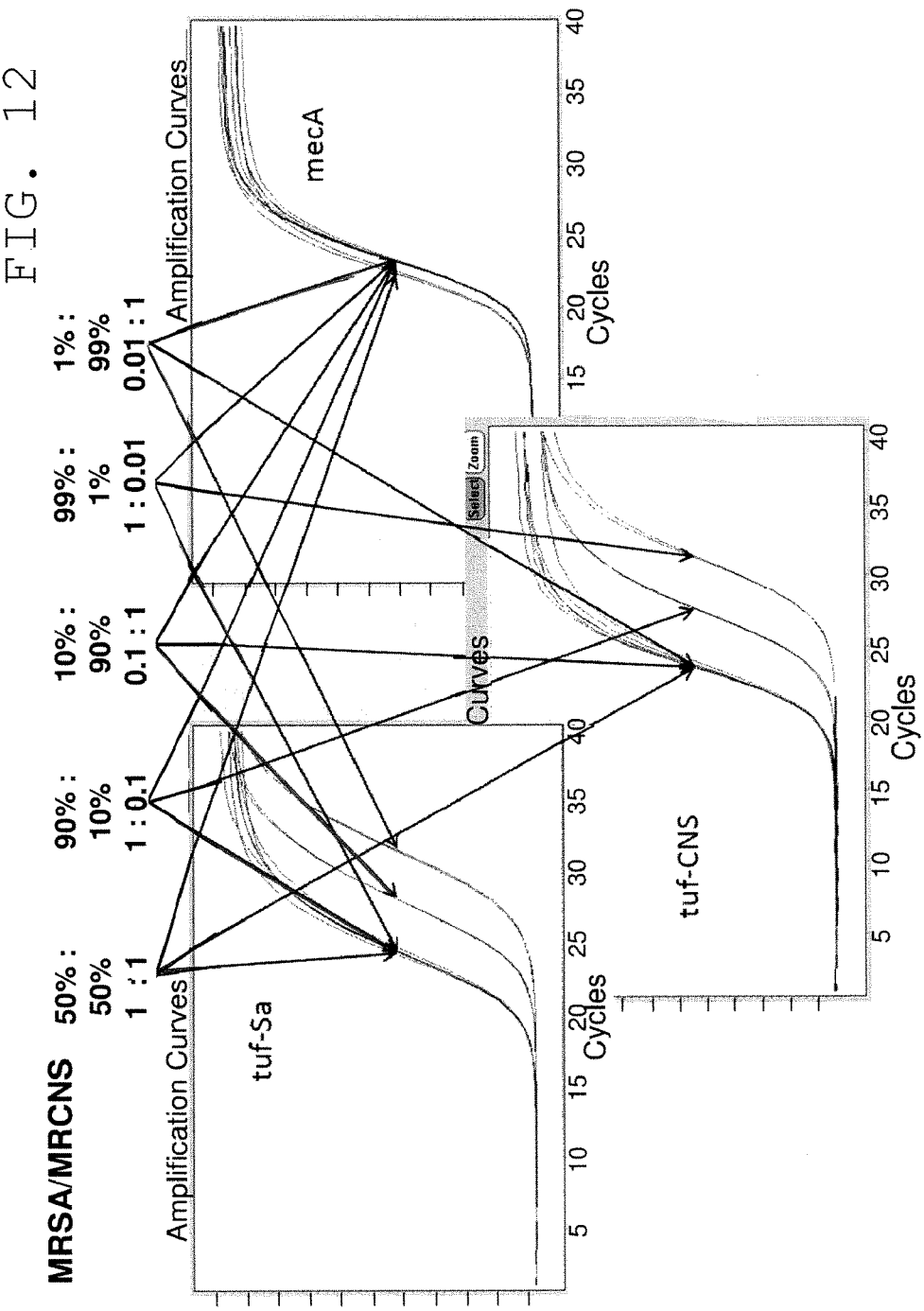
FIG. 12 depicts the results and the amplification curve pattern of a real-time PCR multiplex assay comprising femA-Sa, nuc-Sa, tuf-Sa, tuf-CNS, and mecA assays; the multiplex assay was used to analyze the MRSA/MRCNS group samples including mixtures of MRSA and MRCNS in 1:1, 1:0.1, 0.1:1, 1:0.01, and 0.01:1 ratio. The gradation of the y axis of each graph from bottom to top is 0.074, 0.374, 0.674, 1.274, 1.574, 1.874, 2.174, 2.474, 2.774, and 3.074, respectively for the tuf-Sa graph; 2.269, 3.269, 4.269, 5.269, 6.269, 7.269, 8.269, 9.269, and 10.269, respectively for the mecA graph; and 0.602, 1.602, 2.602, 3.602, 4.602, 5.602, 6.602, 7.602, and 8.602, respectively for the tuf-CNS graph.
Figure 13:
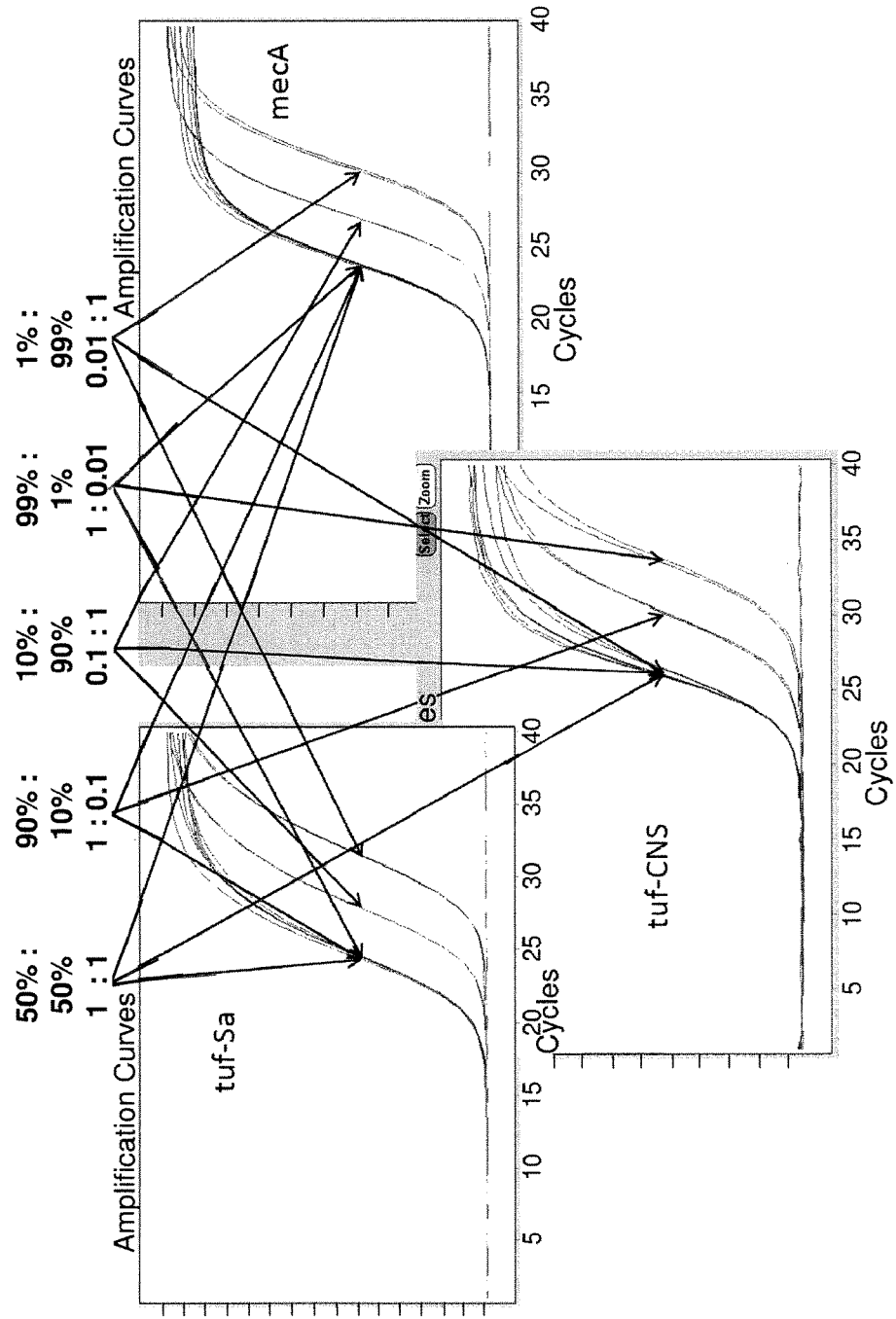
FIG. 13 depicts the results and the amplification curve pattern of a real-time PCR multiplex assay comprising femA-Sa, nuc-Sa, tuf-Sa, tuf-CNS, and mecA assays; the multiplex assay was used to analyze the MRSA/MRCNS group samples including mixtures of MRSA and MSCNS in 1:1, 1:0.1, 0.1:1, 1:0.01, and 0.01:1 ratio. The gradation of the y axis of each graph from bottom to top is 0.024, 0.224, 0.424, 0.624, 0.824, 1.024, 1.224, 1.424, 1.624, 1.824, 2.024, 2.224, 2.424, 2.624, 2.824, and 3.024, respectively for the tuf-Sa graph; 3.191, 4.191, 5.191, 6.191, 7.191, 8.191, 9.191, and 10.191, respectively for the mecA graph; and 0.456, 1.456, 2.456, 3.456, 4.456, 5.456, 6.456, 7.456, and 8.456, respectively for the tuf-CNS graph.

FIG. 6 depicts the results of a set of real-time PCR assays used to analyze the throat swab sample designated TG6775. The assay to detect the presence of nuc resulted in a Ct of 30.2. The assay to detect the presence of *S. aureus* femA resulted in a Ct of 30.1. The assay to detect the presence of mecA resulted in a Ct of 26.8. The assay to detect the presence of the *S. epidermidis* femA gene resulted in a Ct of 34.1. This sample that showed the same pattern of amplification as in FIG. 5, and therefore, may be characterized as containing both MRSA and MRSE. Ct values representing the presence of respective genes from patient samples are summarized in Table 8. Applied Biosystems™ 7900HT real-time PCR platform and Roche's 480 LightCycler were used for Ct value analysis.

TABLE 8

Ct values representing the presence of respective genes

| Sample | 16s | nuc | femA- S. aureus | mecA | femA- S. epi. | tuf allele Ct | tuf allele call | Classification |
|---|---|---|---|---|---|---|---|---|
| TG6582 | 15.7 | 34.9 | 34.5 | 33.8 | UD | 36.1 | S. aureus | MRSA |
| TG6586 | 19.6 | 36.7 | 35.4 | 35.3 | UD | 36.4 | S. aureus | MRSA |
| TG6587 | 15.2 | 34.5 | 33.1 | 32.8 | UD | 34.5 | S. aureus | MRSA |
| TG6588 | 15.0 | 32.0 | 31.3 | 35.2 | 35.9 | 33.3 | S. aureus | MSSA/MRSE |
| TG6590 | 18.0 | UD | UD | UD | 35.9 | UD | UD | MSSE |
| TG6592 | 16.4 | 36.5 | 35.6 | UD | UD | 35.9 | S. aureus | MSSA |
| TG6595 | 18.7 | 30.1 | 29 | UD | UD | 29.2 | S. aureus | MSSA |
| TG6597 | 18.5 | UD | 36.8 | UD | UD | | | MSSA |
| TG6598 | 18.8 | UD | UD | 36.3 | UD | UD | UD | MR in CNS |
| TG6599 | 19.4 | 29.5 | 29 | UD | UD | | | MSSA |
| TG6604 | 17.3 | 33.2 | 33.6 | UD | UD | 36.0 | S. aureus | MSSA |
| TG6607 | 22.4 | 30.1 | 30.3 | 30.8 | 34.6 | 31.6 | S. aureus | MRSA/MSSE* |
|  |  |  |  |  |  | 28.4 | S. epi |  |
| TG6608 | 22.1 | 33.6 | 33.5 | 33.9 | UD | 36.1 | S. aureus | MRSA |
| TG6612 | 24.1 | 30.2 | 30.6 | 29.9 | UD | 31.2 | S. aureus | MRSA |
| TG6615 | 15.9 | 37.3 | 35.7 | UD | UD | 36.9 | S. aureus | MSSA |
| TG6752 | 16.2 | 28.7 | 27.1 | UD | 37.1 | 28.2 | S. aureus | MSSA/MSSE |
| TG6754 | 18.5 | 29.0 | 29.0 | UD | 37.1 | 30.6 | S. aureus | MSSA/MSSE |
| TG6759 | 14.7 | 31.9 | 32.1 | 28.8 | 34.8 | UD | UD | MRSA/MRSE |
| TG6775 | 17.5 | 30.2 | 30.1 | 26.8 | 34.1 | 25.8 | CNS | MRSA/MRSE |
| TG6776 | 24.4 | 36.8 | UD | UD | UD | UD | UD | MSSA |
| TG6777 | 15.7 | 28.7 | 28.0 | UD | UD | 29.6 | S. aureus | MSSA |
| TG6778 | 17.1 | 32.8 | 31.7 | UD | UD | 33.6 | S. aureus | MSSA** |
| TG6779 | 17.1 | 32.9 | 32.1 | UD | UD | 34.1 | S. aureus | MSSA† |

16s is an assay intended to detect the presence of any bacteria.
UD stands for that amplification was undetectable.
CNS stands for Coagulase Negative Staphylococcus.
No SA/No SE means that neither S. aureus nor S. epidermidis was detected.
*stands for nasal swab,
**stands for nasophyaryngeal sample, and
†stands for sputum sample. Remaining samples were throat swabs.

Example 3—Multiplex Real-Time PCR Screening Using Cp Values

This example describes the procedure, equipment, and reagents required to perform a multiplex real-time PCR on the Lightcycler 480 instrument to determine the presence or absence of methicillin resistant and/or susceptible *Staphylococcus aureus* and coagulase negative *Staphylococcus* (CNS) genomic DNA extracted from clinical isolates or specimens using relative Cq values of assays disclosed herein.

Items required: PerfeCTa® MultiPlex qPCR SuperMix (Quanta Cat#95063); Assay primers and probes (Table 1); Molecular biology grade water; Microcentrifuge tubes; Optical reaction plates compatible with real-time instrument; Optical adhesive film and applicator; Micropipettes and tips; Template DNA and appropriate controls (gDNA from MRSA and CNS); Centrifuge with rotors for tubes and plates; Roche Lightcycler 480.

Reaction Preparation:
i. Color compensation: If running the assay for the first time on the instrument, a color compensation file must be generated. Reactions with at least 5 replicates of positive control DNA for each assay in singleplex, tuf-Sa, tuf-CNS, and mecA and 5 total replicates of no template controls must be run. A color compensation file for this multiplex assay need only be generated once. See LC480 User's Manual for details. Prepare color compensation reactions as below.
ii. Assay procedure: (1) calculate volume of mastermix needed (Reaction volume×number samples×1.1); (2) mix reagents to that volume for a final reaction concentration of: 1× PerfeCTa® MultiPlex qPCR SuperMix; 300 nM forward primer; 300 nM reverse primer; 125 nM probe; add water to bring volume so final concentrations are reached upon addition of template; (3) transfer array mastermix into optical reaction plate; (4) add control template: add MRSA DNA template to each tuf-Sa and mecA reaction well; add CNS DNA template to each tuf-CNS reaction well; add water to no template control reaction wells. For subsequent runs on the same instrument, no singleplex assays need to be run. The color compensation file generated previously can be applied to all subsequent multiplex assays using these fluorophores.
iii. Multiplex setup: (1) calculate volume of mastermix needed (reaction volume×number samples×1.1); (2) mix reagents to that volume for a final concentration of: 1× PerfeCTa® MultiPlex qPCR SuperMix; 300 nM each primer; 125 nM each probe; then add water to bring volume so final concentrations are reached upon addition of template; (3) transfer array mastermix into optical reaction plate; (4) add 0.5 to 10 ng DNA extracted from culture, and add more if DNA is extracted from specimens (optimization of template amount may be necessary); seal optical plate with optical adhesive film and spin down the liquid.

Thermal cycling: first, load plate onto instrument; then in LC480 software, create a new experiment with the following program: (1) in Detection Format menu select Multi Color Hydrolysis Probe; (2) select Customize and select colors FAM (483-533), Hex (523-568), and Red 610 (558-610), deselect others; (3) enter proper reaction volume; (4) start run and name file. An exemplary program is illustrated here in Table 9:

TABLE 9

Thermal cycling

Programs

| Program Name | Cycles | Analysis mode |
|---|---|---|
| Hot start | 1 | None |
| Amplification | 40 | Quantification |
| Cooling | 1 | None |

Temperature Targets

| Target (° C.) | Acquisition Mode | Hold (hh:mm:ss) | Ramp Rate (° C./s) | Acquisitions (per ° C.) |
|---|---|---|---|---|
| Hot start | | | | |
| 95 | None | 0:03:00 | 4.8 | |
| Amplification | | | | |
| 95 | None | 0:00:15 | 4.8 | |
| 65 | Single | 0:01:00 | 2.5 | |
| Cooling | | | | |
| 40 | None | 0:00:10 | 2.5 | |

Software setup for color compensation: For the color compensation file generation, designate the color compensation reactions as follows: (1) in Sample Editor, then in Workflow menu, select Color Comp; (2) highlight positive control color comp samples from one assay; (3) choose the detector for that assay in the Dominant Channel pull-down menu; (4) click Make Replicates; (5) repeat for the other two assays; (6) highlight no template controls, and choose Water in the Dominant Channel menu; (7) create a subset which includes all color compensation reaction wells. After the above steps, the setup proceeds with normal software setup for naming samples and designating subsets for samples being run on the multiplex assay.

Analysis:

i. Color compensation: from the Create New Analysis menu, choose Color Compensation, and select the subset of color compensation reactions, then select Calculate; then Save this file to be applied to later analyses of this multiplex assay.

ii. Multiplex: (1) from the Create New Analysis menu, choose AbxQuant/$2^{nd}$ Derivative Max, and select the subset of samples to be analyzed; (2) in the Color Compensation pull-down menu choose In Database, then choose the color compensation file previously generated; (3) select Calculate and select reactions for which data are needed, then export results; (4) select the next color in Filter Comb and Calculate, then select reactions and export results; (5) repeat for last color.

Results: Table 10 presents singleplex and multiplex Cp data collected from a number of samples mixed with different combination and proportions of MRSA, MSSA, MRCNS or MSCNS. For example, in Group 1, MRSA and MSSA were mixed in 5 different ratios: 1:1, 1:0.1, 0.1:1, 1:0.01 and 0.01:1. Each mixture has a duplicate in the same experiment for reproducibility. For Group 1 samples, femA, mecA, nuc, tuf-Sa and tuf-CNS singleplex assays were carried out, and the Cp value for each assay were included in Table 10. Then three multiplex assays were carried out: 1) femA, and mecA; 2) nuc and mecA; and 3) tuf and mecA. The relative Cp value between femA and mecA, nuc and mecA, tuf and mecA were then collected and listed in Table 10. Each expected relative Cp value difference based on the algorithm and singleplex results were projected and listed in Table 10. The observed Cp value difference is the actual data from the multiplex results. The proximity between the expected and the observed Cp value difference reflects the accuracy and reliability of the multiplex assay disclosed herein. Similarly, the singleplex and multiplex assays were carried out for Group 2-6: MRSA/MSCNS, MRSA/MRCNS, MSSA/MRCNS, MRSA/MSSA and MSCNS/MRCNS, with Cp values included in Table 10. Further, the amplification curves of the multiplex assays for Group 1-5, and MRSA/MSCNS, MRSA/MRCNS are shown in FIG. 7-13. In FIG. 7-13, a different combination of tuf-Sa, tuf-CNS, femA, or mecA assay amplification curve patterns are shown for each group comprising sample with different ratios of mixture. These curve patterns are useful for interpreting results of the multiplex assays disclosed herein, and then identify and differentiate MRSA, MSSA, MRCNS, MSCNS in any given sample under the multiplex assay.

TABLE 10

Sa-CNS mixtures femA nuc tuf mecA singleplex and multiplex assays

| | Singleplex assays | | | | | femA mecA multiplex | | | | nuc mecA multiplex | |
|---|---|---|---|---|---|---|---|---|---|---|---|
| | | | | tuf-Sa | tuf-CNS | | | | | | mecA |
| Mix ratio | femA Cp | mecA Cp | nuc Cp | Cp | Cp | femA Cp | mecA Cp | Exp. | Obs. | nuc MP Cp | nuc MP Cp |
| MRSA/MSSA (Group 1) | | | | | | | | | | | |
| 50%:50% | 20.0 | 20.7 | 20.2 | 19.9 | | 19.8 | 20.6 | femA | 0.8 | 20.0 | 20.5 |
| 50%:50% | 19.9 | 20.7 | 20.3 | 19.9 | | 19.8 | 20.5 | 1 Cp lower | Cp lower | 20.1 | 20.5 |
| 90%:10% | 21.0 | 20.7 | 21.2 | 20.9 | | 20.7 | 20.5 | femA < | 0.2 | 21.1 | 20.6 |
| 90%:10% | 21.0 | 20.7 | 21.2 | 20.9 | 35.0 | 20.9 | 20.7 | 1 Cp lower | Cp higher | 21.0 | 20.6 |
| 99%:1% | 21.2 | 20.7 | 21.4 | 21.1 | | 20.9 | 20.6 | femA ~= | .3 Cp | 21.2 | 20.6 |
| 99%:1% | 21.1 | 20.7 | 21.3 | 21.0 | | 21.0 | 20.7 | mecA | higher | 21.2 | 20.6 |
| 10%:90% | 20.8 | 24.1 | 21.0 | 20.7 | 35.0 | 20.8 | 23.9 | femA > | 3.1 | 21.0 | 23.8 |
| 10%:90% | 20.7 | 24.1 | 21.1 | 20.6 | | 20.8 | 23.9 | 3.3 Cp lower | Cp lower | 21.0 | 23.8 |

TABLE 10-continued

Sa-CNS mixtures femA nuc tuf mecA singleplex and multiplex assays

| | | | | | | | | | | | |
|---|---|---|---|---|---|---|---|---|---|---|---|
| 1%:99% | 20.9 | 27.6 | 21.1 | 20.8 | | 20.9 | 27.4 | femA | 6.5 | 21.2 | 27.2 |
| 1%:99% | 20.8 | 27.6 | 21.1 | 20.7 | | 20.8 | 27.3 | ~6.7 Cp lower | Cp lower | 21.2 | 27.2 |
| MRSA/MSCNS (Group 2) | | | | | | | | | | | |
| 50%:50% | 21.1 | 20.7 | 21.5 | 21.1 | 22.9 | 21.0 | 20.7 | femA = | .3 Cp | 21.2 | 20.6 |
| 50%:50% | 21.0 | 20.8 | 21.5 | 21.0 | 22.9 | 20.9 | 20.6 | mecA | higher | 21.1 | 20.6 |
| 90%:10% | 21.1 | 20.8 | 21.5 | 21.1 | 26.2 | 21.0 | 20.7 | femA = | .3 Cp | 21.2 | 20.7 |
| 90%:10% | 21.1 | 20.8 | 21.5 | 21.0 | 26.1 | 20.9 | 20.7 | mecA | higher | 21.2 | 20.7 |
| 99%:1% | 21.0 | 20.8 | 21.5 | 21.1 | 29.7 | 20.9 | 20.7 | femA = | .3 Cp | 21.2 | 20.6 |
| 99%:1% | 21.1 | 20.8 | 21.5 | 21.1 | 29.8 | 21.0 | 20.7 | mecA | higher | 21.2 | 20.7 |
| 10%:90% | 24.5 | 24.1 | 24.7 | 24.6 | 22.8 | 24.4 | 24.0 | femA = | .4 Cp | 24.6 | 24.0 |
| 10%:90% | 24.5 | 24.1 | 24.7 | 24.5 | 22.9 | 24.4 | 24.0 | mecA, +3.3 | higher +3.4 | 24.7 | 24.0 |
| 1%:99% | 27.8 | 27.6 | 28.1 | 27.8 | 22.9 | 27.8 | 27.5 | femA = | .3 Cp | 28.0 | 27.3 |
| 1%:99% | 28.0 | 27.6 | 28.2 | 27.8 | 22.9 | 27.7 | 27.5 | mecA, +3.3 | higher +3.4 | 28.0 | 27.5 |
| MRSA/MRCNS (Group 3) | | | | | | | | | | | |
| 50%:50% | 20.7 | 19.5 | 21.0 | 20.7 | 20.2 | 20.4 | 19.3 | femA | 1.2 | 20.7 | 19.2 |
| 50%:50% | 20.7 | 19.3 | 21.0 | 20.7 | 20.2 | 20.5 | 19.3 | 1 Cp higher | Cp higher | 20.8 | 19.3 |
| 90%:10% | 20.7 | 20.2 | 21.0 | 20.8 | 23.6 | 20.5 | 20.1 | femA < | .4 Cp | 20.8 | 20.1 |
| 90%:10% | 20.7 | 20.2 | 20.9 | 20.7 | 23.7 | 20.5 | 20.1 | 1Cp higher | higher | 20.8 | 20.0 |
| 99%:1% | 20.7 | 20.4 | 20.9 | 20.7 | 27.0 | 20.5 | 20.2 | femA ~= | .3 Cp | 20.8 | 20.1 |
| 99%:1% | 20.6 | 20.3 | 20.9 | 20.7 | 27.0 | 20.5 | 20.2 | mecA | higher | 20.8 | 20.2 |
| 10%:90% | 24.0 | 20.3 | 24.3 | 24.1 | 20.2 | 23.7 | 20.2 | femA > | 3.5 | 24.1 | 20.3 |
| 10%:90% | 24.0 | 20.3 | 24.4 | 24.1 | 20.2 | 23.7 | 20.2 | 3.3 Cp higher | Cp higher | 23.9 | 20.2 |
| 1%:99% | 27.4 | 20.4 | 27.7 | 27.4 | 20.2 | 27.1 | 20.4 | femA | 6.8 | 27.3 | 20.4 |
| 1%:99% | 27.5 | 20.3 | 27.7 | 27.4 | 20.2 | 27.3 | 20.4 | ~6.7 Cp higher | Cp higher | 27.2 | 20.3 |
| MSSA/MRCNS (Group 4) | | | | | | | | | | | |
| 50%:50% | 18.0 | 19.3 | 18.8 | 18.5 | 19.1 | 18.0 | 19.2 | femA = | 1.2 | 18.6 | 19.1 |
| 50%:50% | 18.0 | 19.3 | 18.7 | 18.5 | 19.1 | 18.0 | 19.2 | mecA | Cp lower | 18.7 | 19.2 |
| 90%:10% | 18.0 | 22.7 | 18.7 | 18.4 | 22.6 | 18.1 | 22.5 | femA | 4.4 | 18.6 | 22.3 |
| 90%:10% | 18.0 | 22.7 | 18.8 | 18.3 | 22.6 | 18.1 | 22.6 | 3.3 Cp lower | Cp lower | 18.7 | 22.5 |
| 99%:1% | 18.0 | 26.1 | 18.8 | 18.5 | 25.9 | 18.0 | 26.0 | femA | 8 Cp | 18.7 | 25.8 |
| 99%:1% | 18.0 | 25.9 | 18.7 | 18.3 | 25.9 | 18.1 | 26.0 | 6.7 Cp lower | lower | 18.8 | 25.9 |
| 10%:90% | 21.4 | 19.3 | 22.0 | 21.9 | 19.1 | 21.2 | 19.3 | femA | 1.9 | 21.7 | 19.2 |
| 10%:90% | 21.5 | 19.3 | 22.1 | 21.8 | 19.1 | 21.2 | 19.3 | 3.3 Cp higher | Cp higher | 21.7 | 19.2 |
| 1%:99% | 24.8 | 19.3 | 25.5 | 25.3 | 19.1 | 24.5 | 19.3 | femA | 5.2 | 25.0 | 19.3 |
| 1%:99% | 24.8 | 19.3 | 25.4 | 25.2 | 19.0 | 24.6 | 19.3 | 6.7 Cp higher | Cp higher | 25.1 | 19.3 |
| MRSA/MSSA (Group 5) | | | | | | | | | | | |
| 50%:50% | 17.9 | | 18.8 | 18.5 | 18.6 | 18.1 | 34.3 | mecA | mecA | 18.7 | 34.3 |
| 50%:50% | 18.0 | | 18.8 | 18.5 | 18.5 | 18.1 | 34.5 | UD | late | 18.7 | 34.6 |
| 90%:10% | 17.9 | | 18.8 | 18.6 | 22.0 | 18.1 | | femA | femA | 18.7 | 35.4 |
| 90%:10% | 18.0 | | 18.8 | 18.5 | 21.9 | 18.1 | 37.3 | same, mecA UD | same, mecA late | 18.7 | 35.5 |
| 99%:1% | 17.9 | | 18.7 | 18.5 | 25.3 | 18.1 | | femA | femA | 18.8 | |
| 99%:1% | 18.1 | | 18.8 | 18.5 | 25.3 | 18.1 | | same, mecA UD | same, mecA UD | 18.8 | |
| 10%:90% | 21.4 | | 22.1 | 21.9 | 18.6 | 21.5 | 34.9 | femA +3.3 Cp, mecA UD | femA +3.4, mecA late | 22.0 | 33.8 |
| 10%:90% | 21.5 | | 22.1 | 21.9 | 18.6 | 21.5 | 34.6 | | | 22.0 | 33.9 |

TABLE 10-continued

Sa-CNS mixtures femA nuc tuf mecA singleplex and multiplex assays

| | | | | | | | | | | |
|---|---|---|---|---|---|---|---|---|---|---|
| 1%:99% | 24.8 | 25.5 | 25.2 | 18.6 | 24.9 | 34.1 | femA | femA | 25.3 | 34.0 |
| 1%:99% | 24.8 | 25.3 | 25.3 | 18.5 | 24.9 | 33.8 | +3.3 Cp, mecA UD | +3.4, mecA late | 25.3 | 34.5 |

MSCNS/MRCNS
(Group 6)

| | | | |
|---|---|---|---|
| 50%:50% | 19.2 | | 17.7 |
| 50%:50% | 19.2 | 35.0 | 17.7 |
| 90%:10% | 22.7 | | 18.4 |
| 90%:10% | 22.7 | | 18.5 |
| 99%:1% | 26.0 | | 18.5 |
| 99%:1% | 26.0 | | 18.5 |
| 10%:90% | 19.2 | | 18.9 |
| 10%:90% | 19.2 | | 18.9 |
| 1%:99% | 19.2 | | 19.1 |
| 1%:99% | 19.2 | | 19.0 |

| | nuc mecA multiplex | | tuf-Sa | mecA | tuf-CNS | tuf mecA multiplex | |
|---|---|---|---|---|---|---|---|
| Mix ratio | Exp. | Obs. | Cp | Cp | Cp | Exp. | Obs. |

MRSA/MSSA
(Group 1)

| | | | | | | | |
|---|---|---|---|---|---|---|---|
| 50%:50% | nuc | 0.5 | 19.8 | 20.6 | | Sa 1 | Sa .8 |
| 50%:50% | 1.0 Cp lower | Cp lower | 19.9 | 20.6 | 35.0 | Cp lower mecA, CNS UD | Cp lower mecA, CNS UD |
| 90%:10% | nuc < | .5 Cp higher | 20.7 | 20.6 | | Sa < 1 Cp lower mecA, CNS UD | Sa .2 Cp higher mecA, CNS UD |
| 90%:10% | 1 Cp lower | | 20.7 | 20.5 | | | |
| 99%:1% | nuc ~= mecA | .6 Cp higher | 20.8 | 20.6 | | Sa ~= mecA, CNS UD | Sa .3 Cp higher mecA, CNS UD |
| 99%:1% | | | 20.8 | 20.5 | | | |
| 10%:90% | nuc > | 2.8 | 20.6 | 23.8 | 35.0 | Sa > 3.3 Cp lower mecA, CNS UD | Sa 3.2 Cp lower mecA, CNS UD |
| 10%:90% | 3.3 Cp lower | Cp lower | 20.7 | 23.9 | | | |
| 1%:99% | nuc ~6.7 Cp lower | 6 Cp lower | 20.8 | 27.2 | 35.0 | Sa ~6.7 Cp lower mecA, CNS UD | Sa 6.4 Cp lower mecA, CNS late |
| 1%:99% | | | 20.9 | 27.2 | 35.0 | | |

MRSA/MSCNS
(Group 2)

| | | | | | | | |
|---|---|---|---|---|---|---|---|
| 50%:50% | nuc = mecA | .6 Cp higher | 20.9 | 20.6 | 22.8 | Sa = mecA = CNS | Sa .3 Cp > mecA, CNS 2.2 Cp > mecA |
| 50%:50% | | | 20.8 | 20.6 | 22.8 | | |
| 90%:10% | nuc = mecA | .5 Cp higher | 20.9 | 20.6 | 26.4 | Sa = mecA, CNS 3.3 Cp higher | Sa .3 Cp > mecA, CNS 5.8 Cp > mecA |
| 90%:10% | | | 21.0 | 20.7 | 26.6 | | |

TABLE 10-continued

Sa-CNS mixtures femA nuc tuf mecA singleplex and multiplex assays

| | | | | | | | |
|---|---|---|---|---|---|---|---|
| 99%:1% | nuc = | .6 Cp | 20.9 | 20.6 | 29.9 | Sa = | Sa .3 |
| 99%:1% | mecA | higher | 20.9 | 20.6 | 30.0 | mecA, | Cp > |
| | | | | | | CNS | mecA, |
| | | | | | | 6.7 | CNS |
| | | | | | | Cp | 9.3 Cp > |
| | | | | | | higher | mecA |
| 10%:90% | nuc = | .6 Cp | 24.2 | 23.9 | 22.8 | Sa = mecA, | Sa .3 |
| 10%:90% | mecA, | higher, | 24.2 | 23.9 | 22.8 | CNS | Cp > |
| | +3.3 | +3.4 | | | | 3.3 | mecA, |
| | | | | | | Cp | CNS |
| | | | | | | lower | 1.1 Cp < |
| | | | | | | | mecA |
| 1%:99% | nuc = | .6 Cp | 27.8 | 27.2 | 22.9 | Sa = mecA, | Sa .6 |
| 1%:99% | mecA, | higher, | 27.7 | 27.1 | 22.9 | CNS | Cp > |
| | +3.3 | +3.4 | | | | 6.7 | mecA, |
| | | | | | | Cp | CNS |
| | | | | | | lower | 4.3 Cp < |
| | | | | | | | mecA |
| MRSA/MRCNS (Group 3) | | | | | | | |
| 50%:50% | nuc 1 | 1.5 | 20.3 | 19.2 | 20.2 | (Sa = | (Sa = |
| 50%:50% | Cp | Cp | 20.4 | 19.2 | 20.2 | CNS) | CNS) 1 |
| | higher | higher | | | | 1 Cp > | Cp > |
| | | | | | | mecA | mecA |
| 90%:10% | nuc < | .8 Cp | 20.4 | 20.0 | 23.7 | Sa < 1 | Sa .4 |
| 90%:10% | 1Cp | higher | 20.4 | 20.0 | 23.7 | Cp > | Cp > |
| | higher | | | | | mecA, | mecA, |
| | | | | | | CNS | CNS |
| | | | | | | 3.3 | 3.3 Cp > |
| | | | | | | Cp > | Sa |
| | | | | | | Sa | |
| 99%:1% | nuc ~= | .7 Cp | 20.3 | 20.0 | 27.3 | Sa ~= | Sa .3 |
| 99%:1% | mecA | higher | 20.4 | 20.0 | 27.4 | mecA, | Cp > |
| | | | | | | CNS | mecA, |
| | | | | | | 6.7 | CNS 7 |
| | | | | | | Cp > | Cp > |
| | | | | | | Sa | Sa |
| 10%:90% | nuc > | 3.8 | 23.8 | 20.0 | 20.2 | Sa > | Sa 3.8 |
| 10%:90% | 3.3 | Cp | 23.7 | 20.0 | 20.2 | 3.3 | Cp > |
| | Cp | higher | | | | Cp > | mecA, |
| | higher | | | | | mecA, | CNS .2 |
| | | | | | | CNS < | Cp > |
| | | | | | | 1 Cp > | mecA |
| | | | | | | mecA | |
| 1%:99% | nuc | 6.9 | 27.3 | 20.1 | 20.2 | Sa | Sa 7.2 |
| 1%:99% | ~6.7 | Cp | 27.5 | 20.2 | 20.2 | ~6.7 | Cp > |
| | Cp | higher | | | | Cp > | mecA, |
| | higher | | | | | mecA, | CNS = |
| | | | | | | CNS ~= | mecA |
| | | | | | | mecA | |
| MSSA/MRCNS (Group 4) | | | | | | | |
| 50%:50% | nuc = | .5 Cp | 18.1 | 19.0 | 19.0 | Sa = | mecA = |
| 50%:50% | mecA | lower | 18.2 | 19.0 | 19.0 | mecA = | CNS, |
| | | | | | | CNS | Sa .9 |
| | | | | | | | Cp |
| | | | | | | | lower |
| 90%:10% | nuc | 3.7 | 18.5 | 22.5 | 22.6 | (mecA = | (mecA = |
| 90%:10% | 3.3 | Cp | 18.5 | 22.5 | 22.6 | CNS) | CNS) |
| | Cp | lower | | | | 3.3 | 4 Cp > |
| | lower | | | | | Cp > | Sa |
| | | | | | | Sa | |
| 99%:1% | nuc | 7.1 | 18.6 | 25.8 | 26.0 | (mecA = | (mecA |
| 99%:1% | 6.7 | Cp | 18.5 | 25.7 | 26.0 | CNS) | .2 Cp < |
| | Cp | lower | | | | 6.7 | CNS) |
| | lower | | | | | Cp > | 7.3 Cp > |
| | | | | | | Sa | Sa |
| 10%:90% | nuc | 2.5 | 21.5 | 19.1 | 19.1 | (mecA = | (mecA = |
| 10%:90% | 3.3 | Cp | 21.5 | 19.1 | 19.1 | CNS) | CNS) |
| | Cp | higher | | | | 3.3 | 2.4 Cp < |
| | higher | | | | | Cp < | Sa |
| | | | | | | Sa | |

TABLE 10-continued

Sa-CNS mixtures femA nuc tuf mecA singleplex and multiplex assays

| | | | | | | | |
|---|---|---|---|---|---|---|---|
| 1%:99% | nuc | 5.7 | 25.1 | 19.0 | 19.1 | (mecA = | (mecA = |
| 1%:99% | 6.7 Cp higher | Cp higher | 25.1 | 19.0 | 19.1 | CNS) 6.7 Cp < Sa | CNS) 6.1 Cp < Sa |
| MRSA/MSSA (Group 5) | | | | | | | |
| 50%:50% | mecA | mecA | 18.2 | 35.0 | 18.4 | Sa = | Sa .2 |
| 50%:50% | UD | late | 18.3 | 35.0 | 18.5 | CNS, mecA UD | Cp < CNS, mecA late |
| 90%:10% | nuc | nuc | 18.5 | | 22.0 | Sa 3.3 | Sa 3.5 |
| 90%:10% | same, mecA UD | same, mecA late | 18.5 | 35.0 | 22.0 | Cp < CNS, mecA UD | Cp < CNS, mecA UD |
| 99%:1% | nuc | nuc | 18.5 | | 25.5 | Sa 6.7 | Sa 7 |
| 99%:1% | same, mecA UD | +.1 Cp, mecA UD | 18.5 | | 25.5 | Cp < CNS, mecA UD | Cp < CNS, mecA UD |
| 10%:90% | nuc | nuc | 21.8 | 35.0 | 18.6 | Sa 3.3 | Sa 3.2 |
| 10%:90% | +3.3 Cp, mecA UD | +3.2 Cp, mecA late | 21.8 | 34.6 | 18.6 | Cp > CNS, mecA UD | Cp > CNS, mecA late |
| 1%:99% | nuc | nuc | 25.2 | 35.0 | 18.5 | Sa 6.7 | Sa 6.7 |
| 1%:99% | +3.3 Cp, mecA UD | +3.3 Cp, mecA late | 25.2 | 35.0 | 18.5 | Cp > CNS, mecA UD | Cp > CNS, mecA late |
| MSCNS/MRCNS (Group 6) | | | | | | | |
| 50%:50% | | | | 19.0 | 17.8 | mecA | mecA |
| 50%:50% | | | 35.0 | 22.4 | 17.8 | 1 Cp > CNS, Sa UD | 1.2 Cp > CNS, Sa UD |
| 90%:10% | | | | 22.4 | 18.5 | mecA | mecA |
| 90%:10% | | | | 22.4 | 18.5 | >3.3 Cp > CNS, Sa UD | 3.9 Cp > CNS, Sa UD |
| 99%:1% | | | | 25.8 | 18.6 | mecA | mecA |
| 99%:1% | | | | 25.8 | 18.6 | ~6.7 Cp > CNS, Sa UD | 7.2 Cp > CNS, Sa UD |
| 10%:90% | | | | 19.1 | 18.9 | mecA < | mecA |
| 10%:90% | | | | 19.1 | 18.9 | 1 Cp > CNS, Sa UD | .2 Cp > CNS, Sa UD |
| 1%:99% | | | | 19.0 | 19.1 | mecA ~ = | mecA = |
| 1%:99% | | | | 19.1 | 19.1 | CNS, Sa UD | CNS, Sa UD |

Exp.—Expected
Obs.—Observed

Interpretation: Determination of species and mecA carriage with the multiplex assay depends on relative Cp values among the multiple assay results. mecA Cp should be equal to the Cp of the assay targeting the species carrying it. In an exemplary application, using relative Cq values of assays targeting tuf in *S. aureus*, tuf in CNS, and mecA. If both species carry mecA, the mecA Cp should be lower than both species assays. Some nonlimiting examples of results and interpretation are presented in Table 11:

TABLE 11

Using relative Cp value to interpret the multiplex assay results

| Possible Result | Likely scenario |
|---|---|
| 1 tuf-CNS Cp = tuf-Sa Cp; and mecA is 1 Cp lower; | MRCNS and MRSA are present. |

TABLE 11-continued

Using relative Cp value to interpret the multiplex assay results

| Possible Result | Likely scenario |
| --- | --- |
| 2 tuf-CNS Cp = mecA Cp; and tuf-Sa Cp is lower or within 3 Cp higher; | MRCNS and MSSA are present. |
| 3 tuf-Sa Cp = mecA Cp; and tuf-CNS Cp is lower or within 3 Cp higher; | MRSA and MSCNS are present. |
| 4 tuf-CNS Cp = mecA Cp; and tuf-Sa is > 3 Cp higher; | MRCNS and MRSA, or MRCNS and MSSA are present. |
| 5 tuf-Sa Cp = mecA Cp, and tuf-CNS is > 3 Cp higher; | MRSA and MRCNS, or MRSA and MSCNS are present |
| 6 tuf-Sa Cp = tuf-CNS Cp = mecA; | MRCNS and MSSA, or MSCNS and MRSA are present. |

Example 4—Additional Sequences that can be Used to Develop Similar Assays to Detect the Presence of MRSA Additional sequences that can be used to develop similar assays as disclosed herein to detect the presence of MRSA further include the following: SEQ ID NO. 19—*S. aureus* nuc, SEQ ID NO. 20—*S. aureus* femA, SEQ ID NO. 21—*S. epidermidis* femA, SEQ ID NO. 22—*S. aureus* tuf, SEQ ID NO. 23 *S. capitis* tuf, SEQ ID NO. 24—*S. epidermidis* tuf, SEQ ID NO. 25—*S. haemolyticus* tuf, SEQ ID NO. 26. *S. hominis* tuf, SEQ ID NO. 27—*S. lugdunensis* tuf, SEQ ID NO. 28—*S. simulans* tuf, SEQ ID NO. 29—*S. warneri* tuf, and SEQ ID NO. 30—*S. aureus* mecA, which are detailed in the Sequence Listings.

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A multiplex assay for identifying and differentiating combinations of methicillin-resistant *Staphylococcus aureus* (MRSA), methicillin-sensitive *Staphylococcus aureus* (MSSA), methicillin-resistant *Staphylococcus epidermidis* (MRSE), methicillin-sensitive *Staphylococcus epidermidis* (MSSE), methicillin-resistant coagulase-negative staphylococci (MRCNS), and/or methicillin-sensitive coagulase-negative staphylococci (MSCNS) in a sample, comprising:
performing a PCR-based mecA assay, a PCR-based tuf-Sa assay, and at least one PCR-based assay selected from a femA Se assay and a tuf-CNS assay;
wherein said PCR-based assays comprise at least one target gene and at least one reference gene; the primers for the mecA assay comprise SEQ ID NO: 16 and 17 and the probe for the mecA assay comprises SEQ ID NO: 18; the primers for the tuf-Sa assay comprise SEQ ID NO: 10 and 11 and the probe for the tuf-Sa assay comprises SEQ ID NO: 12; the primers for the femA-Se assay comprise SEQ ID NO: 7 and 8 and the probe for the femA-Se assay comprises SEQ ID NO: 9; and the primers for the tuf-CNS assay comprise SEQ ID NO: 13 and 14 and the probe for the tuf-CNS assay comprises SEQ ID NO: 15; and
wherein the PCR-based assays are performed with quantitative PCR, quantitative real time PCR, quantitative reverse transcription PCR, or quantitative real time reverse transcription PCR.

2. The multiplex assay of claim 1, further comprising at least one PCR-based assay to detect the presence or absence of a nuc-Sa gene or a femA-Sa gene.

3. The multiplex assay of claim 2, wherein the primer set associated with the PCR-based nuc-Sa assay comprises SEQ ID NO: 1 and 2.

4. The multiplex assay of claim 3, further comprising a probe associated with the PCR-based nuc-Sa assay comprising SEQ ID NO: 3.

5. The multiplex assay of claim 2, wherein the primer set associated with the PCR-based femA-Sa assay comprises SEQ ID NO: 4 and 5.

6. The multiplex assay of claim 5, further comprising a probe associated with the PCR-based femA-Sa assay comprising SEQ ID NO: 6.

7. The multiplex assay of claim 1, wherein the PCR-based assays are configured to analyze expression of the target gene in relation to the reference gene according to relative quantification of crossing points values or cycle threshold values using additive effects of relative cycle threshold values contributed from different strains within the sample.

8. The multiplex assay of claim 1, wherein the PCR-based mecA assay, the PCR-based tuf-Sa assay, and the PCR-based femA-Se assay are performed.

9. The multiplex assay of claim 1, wherein the PCR-based mecA assay, the PCR-based tuf-Sa assay, and the PCR-based tuf-CNS assay are performed.

10. The multiplex assay of claim 1, wherein the PCR-based assays are performed with quantitative real time PCR.

11. The multiplex assay of claim 1, wherein the step of performing the PCR-based assays further comprises:
 a. determining the presence of a mecA gene within the sample to detect the presence of at least one of MRSA, MRCNS and MRSE;
 b. determining the presence of a tuf-*S. aureus* gene to detect the presence of at least one of MRSA and MSSA;
 c. determining the presence of a tuf-CNS assay gene to detect the presence of at least one of MRCNS and MSCNS; and/or
 d. determining the presence of a femA-*S. epidermis* gene to detect the presence of at least one of MRSE and MSSE.

12. A method for identifying combinations of MRSA, MSSA, MRSE, MSSE, MRCNS, and/or MSCNS in a sample, comprising
 a. obtaining a sample;
 b. screening the sample by conducting a PCR-based mecA assay, a PCR-based tuf-Sa assay, and at least one PCR-based assay selected from a femA-Se assay and a tuf-CNS assay,
  wherein the PCR-based assays comprise at least one target gene and at least one reference gene; the primers for the mecA assay comprise SEQ ID NO: 16 and 17 and the probe for the mecA assay comprises SEQ ID NO: 18; the primers for the tuf-Sa assay comprise SEQ ID NO: 10 and 11 and the probe for the tuf-Sa assay comprises SEQ ID NO: 12; the primers for the femA-Se assay comprise SEQ ID NO: 7 and 8 and the probe for the femA-Se assay comprises SEQ ID NO: 9; and the primers for the tuf-CNS assay comprise SEQ ID NO: 13 and 14 and the probe for the tuf-CNS assay comprises SEQ ID NO: 15; and
  wherein the PCR-based assays are performed with quantitative PCR, quantitative real time PCR, quantitative reverse transcription PCR, or quantitative real time reverse transcription PCR;
 c. analyzing results obtained from the PCR-based assays to determine the presence or absence of a mecA gene, a tuf-*S. aureus* gene, and at least one gene selected from a femA-*S. epidermis* gene and a tuf-CNS gene;
 d. identifying combinations of MRSA, MSSA, MRSE, MSSE, MRCNS and/or MSCNS based on the results of the PCR-based assays.

13. The method of claim 12, wherein the step of analyzing results obtained from the PCR-based assays further comprises:

a. determining the presence of said mecA gene within the sample to detect the presence of at least one of MRSA, MRCNS and MRSE;
b. determining the presence of said tuf-*S. aureus* gene to detect the presence of at least one of MRSA and MSSA;
c. determining the presence of said tuf-CNS assay gene to detect the presence of at least one of MRCNS and MSCNS; and/or
d. determining the presence of said femA-*S. epidermis* gene to detect the presence of at least one of MRSE and MSSE.

14. The method of claim 12, wherein the PCR-based assays are configured to analyze expression of the target gene in relation to the reference gene according to relative quantification of crossing points values or cycle threshold values using additive effects of relative cycle threshold values contributed from different strains within the sample.

15. The method of claim 12, wherein screening the sample comprises conducting the PCR-based mecA assay, the PCR-based tuf-Sa assay, and the PCR-based femA-Se assay.

16. The method of claim 12, wherein screening the sample comprises conducting the PCR-based mecA assay, the PCR-based tuf-Sa assay, and the PCR-based tuf-CNS assay.

17. The method of claim 12, wherein the PCR-based assays are performed with quantitative real time PCR.

18. The method of claim 12, wherein the sample is a fluid sample comprising peripheral blood, lymph fluid, ascites, serous fluid, pleural effusion, sputum, bronchial wash, bronchioalveolar lavage fluid (BALF), cerebrospinal fluid, semen, amniotic fluid, lacrimal fluid, stool, or urine.

19. The method of claim 12, wherein the sample is derived from an agricultural or environmental source.

* * * * *

UNITED STATES PATENT AND TRADEMARK OFFICE
CERTIFICATE OF CORRECTION

PATENT NO. : 10,100,368 B2
APPLICATION NO. : 13/051755
DATED : October 16, 2018
INVENTOR(S) : Elizabeth Driebe et al.

Page 1 of 1

It is certified that error appears in the above-identified patent and that said Letters Patent is hereby corrected as shown below:

In the Specification

Column 1, Line 15, insert the following text: --STATEMENT REGARDING FEDERALLY SPONSORED RESEARCH--

Column 5, Line 31, cancel the text "invention if it is able of binding to its complimentary", and insert the following text: --invention if it is capable of binding to its complimentary--

Column 6, Line 43, cancel the text ",for example_____,"

Column 20, Line 11, cancel the text "Table 7 A-D.", and insert the following text: --Tables 7 A-D--

Column 20, Line 57, cancel the text "The above assays shown in Table 2-7 may be used", and insert the following text: --The above assays shown in Tables 2-7 may be used--

In the Claims

Column 55, Line 65, Claim 8, cancel the text "The multiplex assay of cliam 1, wherein the PCR-based mecA assay, the PCR-based tuf-Sa assay, and the PCR-basedfemA-Se assay are performed.", and insert the following text: --The multiplex assay of claim 1, wherein the PCR-based mecA assay, the PCR-based tuf-Sa assay, and the PCR-based femA-Se assay are performed.--

Column 57, Line 18, Claim 15, cancel the text "The method of claim 12, wherein screening the sample comprises conducting the PCR-based mecA assay, the PCR-based tuf-Sa assay, and the PCR-basedfemA-Se assay.", and insert the following text: --The method of claim 12, wherein screening the sample comprises conducting the PCR-based mecA assay, the PCR-based tuf-Sa assay, and the PCR-based femA-Se assay.--

Signed and Sealed this
Twenty-second Day of January, 2019

Andrei Iancu
*Director of the United States Patent and Trademark Office*